United States Patent
Hasegawa et al.

(10) Patent No.: US 9,096,566 B2
(45) Date of Patent: Aug. 4, 2015

(54) ESTER GROUP-CONTAINING TETRACARBOXYLIC ACID DIANHYDRIDE, POLYESTER POLYIMIDE PRECURSOR, POLYESTERIMIDE, AND METHODS FOR PRODUCING SAME

(75) Inventors: Masatoshi Hasegawa, Funabashi (JP); Tadashi Hiramine, Wakayama (JP); Yuuki Hashimoto, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 228 days.

(21) Appl. No.: 13/148,764

(22) PCT Filed: Feb. 12, 2010

(86) PCT No.: PCT/JP2010/052092
§ 371 (c)(1),
(2), (4) Date: Oct. 19, 2011

(87) PCT Pub. No.: WO2010/093021
PCT Pub. Date: Aug. 19, 2010

(65) Prior Publication Data
US 2012/0029164 A1 Feb. 2, 2012

(30) Foreign Application Priority Data

Feb. 12, 2009 (JP) .................. 2009-030494
Jun. 30, 2009 (JP) .................. 2009-156229

(51) Int. Cl.
| | | |
|---|---|---|
| C08G 73/16 | (2006.01) | |
| C07D 307/89 | (2006.01) | |
| C07D 209/48 | (2006.01) | |
| H05K 1/03 | (2006.01) | |

(52) U.S. Cl.
CPC ............ *C07D 307/89* (2013.01); *C07D 209/48* (2013.01); *C08G 73/16* (2013.01); *H05K 1/0346* (2013.01); *H05K 1/0393* (2013.01); *H05K 2201/012* (2013.01); *H05K 2201/0154* (2013.01)

(58) Field of Classification Search
CPC ..................... C08G 73/16; H05K 2201/0154
USPC .......................... 528/353; 549/242
See application file for complete search history.

(56) References Cited

U.S. PATENT DOCUMENTS

2004/0038054 A1 2/2004 Wang et al.
2009/0306329 A1 12/2009 Hasegawa

FOREIGN PATENT DOCUMENTS

| JP | 4-29986 | | 1/1992 |
|---|---|---|---|
| JP | 9-258229 | A | 10/1997 |
| JP | 10-70157 | A | 3/1998 |
| JP | 11-263785 | A | 9/1999 |
| JP | 2004-79826 | A | 3/2004 |
| JP | 2005-298623 | A | 10/2005 |
| JP | 2006-13419 | A | 1/2006 |
| JP | 2006-336011 | A | 12/2006 |
| WO | WO 2008/091011 | A1 | 7/2008 |

OTHER PUBLICATIONS

Masatoshi Hasegawa et al., Spontaneous Molecular Orientation of Polyimides Induced by Thermal Imidization. 2. In-Plane Orientation, Macromolecules, 29, 7897-7909 (1996).
Sek, D et al., New semiladder polymers: 1. Synthesis and properties of new poly (ester imidazopyrrolone)s, Polymer, 1998, vol. 39, No. 26, p. 7001-7008.
High Performance Polymers, 18, 697 (2006).
K. Koseki et al., "Poly(ester imide)s Derived from Trimellitic Anhydride (3). Low CTE characteristics, thermo-and solution-processability," Polymer Preprints, Japan, vol. 53, No. 2 (2004) p. 4115.
The Office Action issued by the U.S. Patent and Trademark Office on Jun. 10, 2011 for the corresponding U.S. Appl. No. 12/523,856.

*Primary Examiner* — Gregory Listvoyb
(74) *Attorney, Agent, or Firm* — Knobbe, Martens, Olson & Bear LLP

(57) ABSTRACT

A polyesterimide having a repeating unit expressed by formula (3) is useful for FPC substrates, COF substrates and TAB substrate materials, especially as FPC substrate materials:

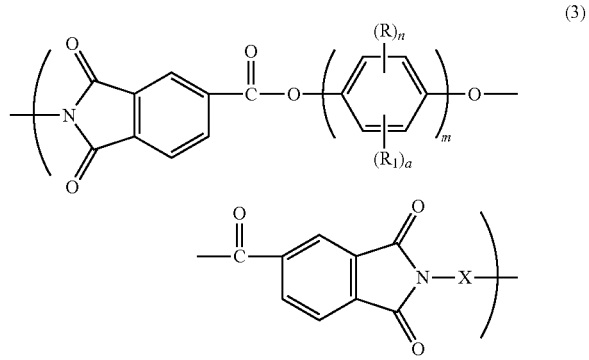

wherein R represents a phenyl group, $R_1$ represents an alkyl group with 1 to 6 carbon atoms or alkoxy group with 1 to 6 carbon atoms, n each independently takes a value of 0 to 4, a each independently takes a value of 0 to 4, and m represents an integer of 2 to 4, where not all n's are 0 at the same time and $0 \le n+a \le 4$ is satisfied by each phenylene group, and X is a divalent aromatic group and/or aliphatic group.

11 Claims, 13 Drawing Sheets

[Fig. 1]
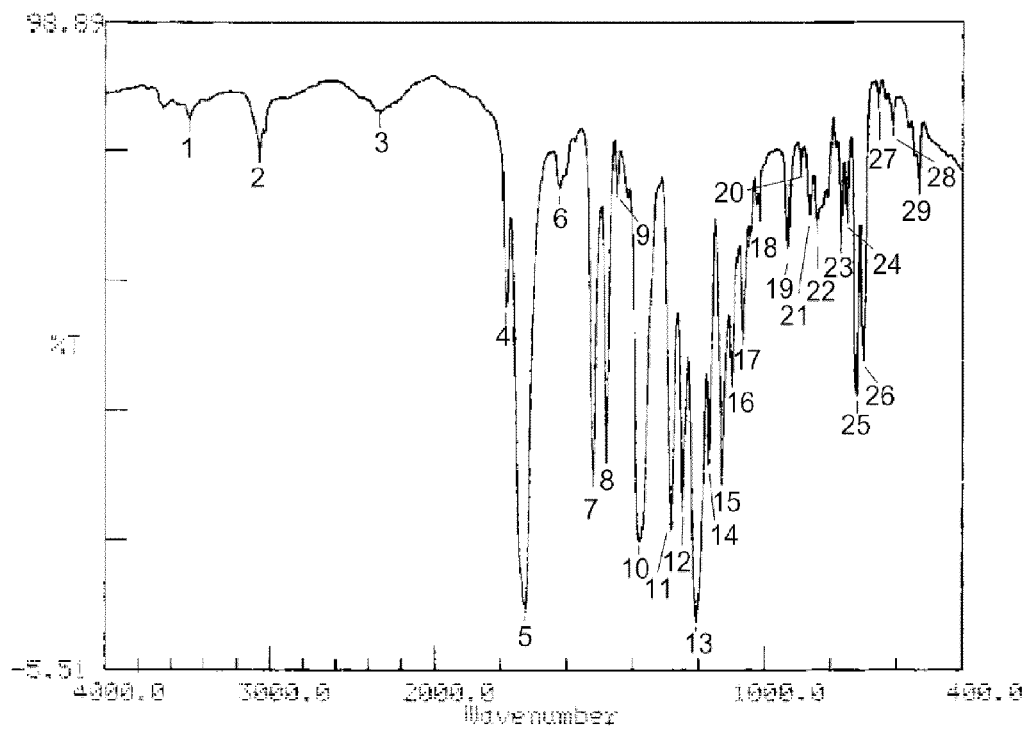

[Fig. 2]
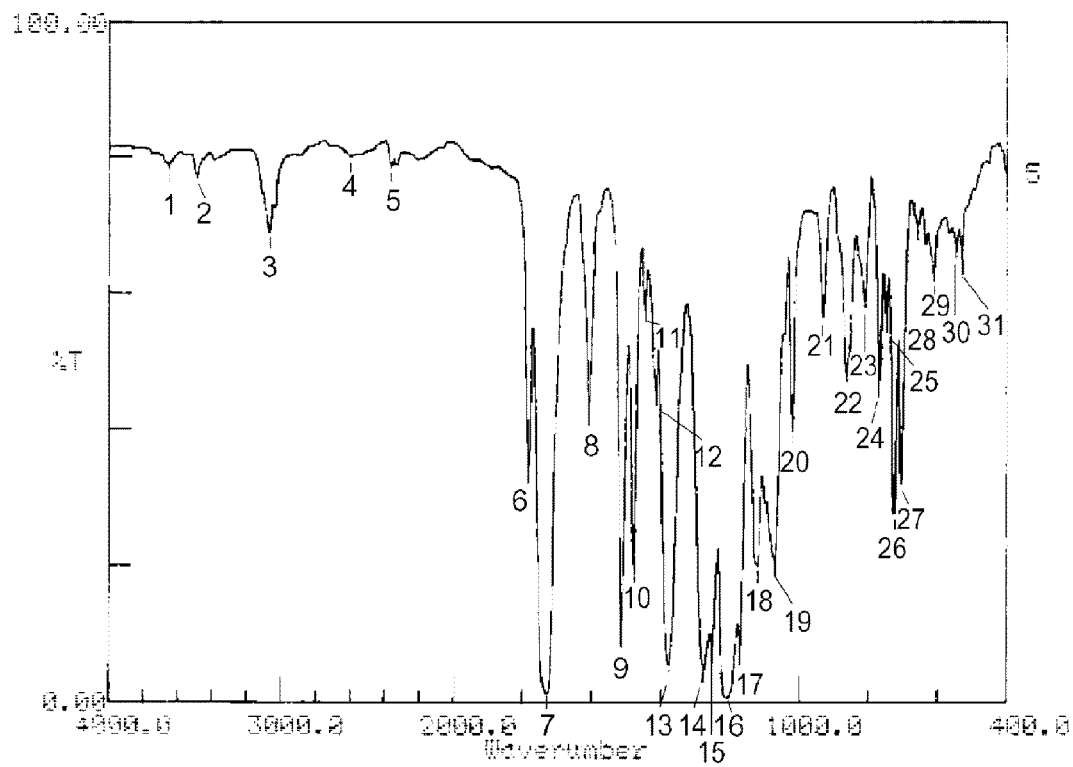

[Fig. 3]
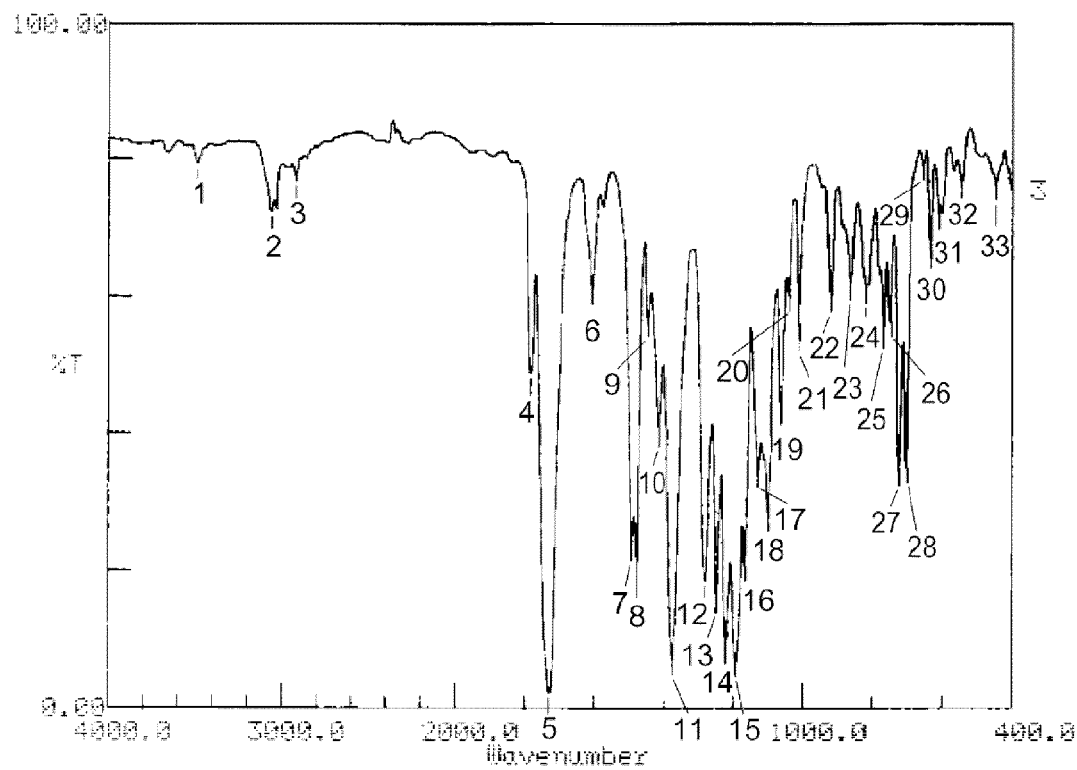

[Fig. 4]
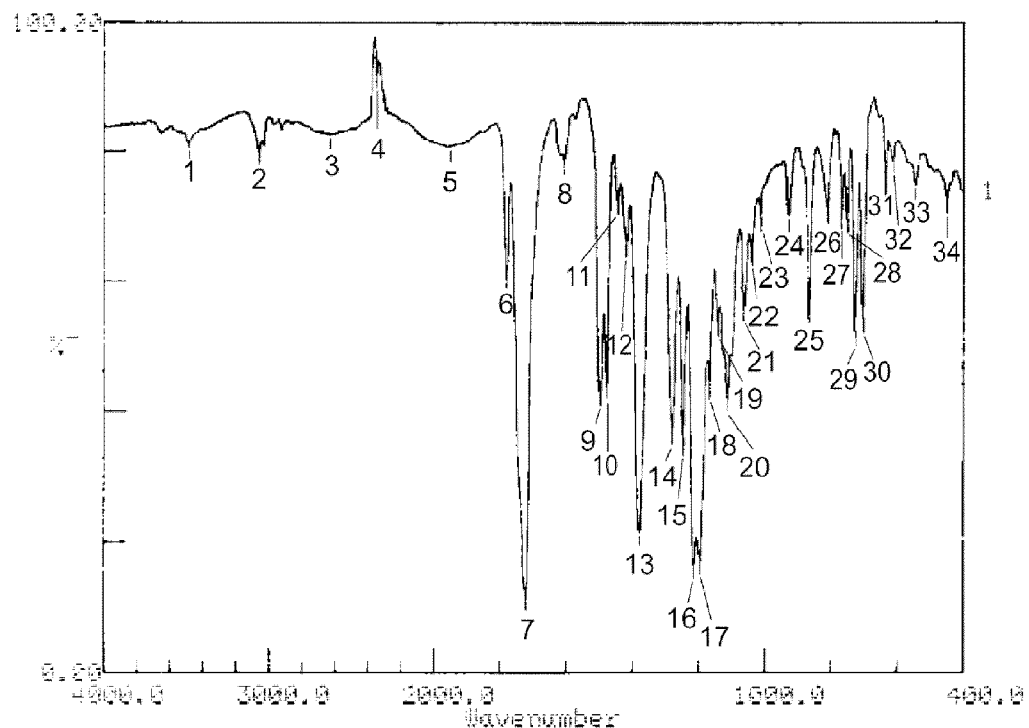

[Fig. 5]
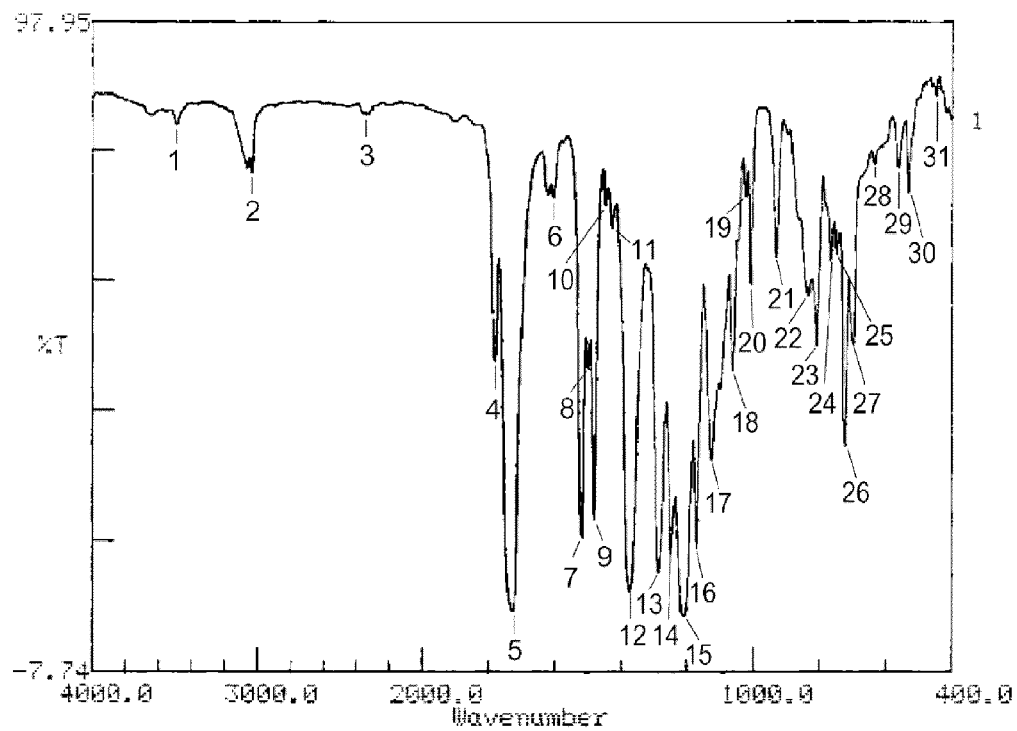

[Fig. 6]
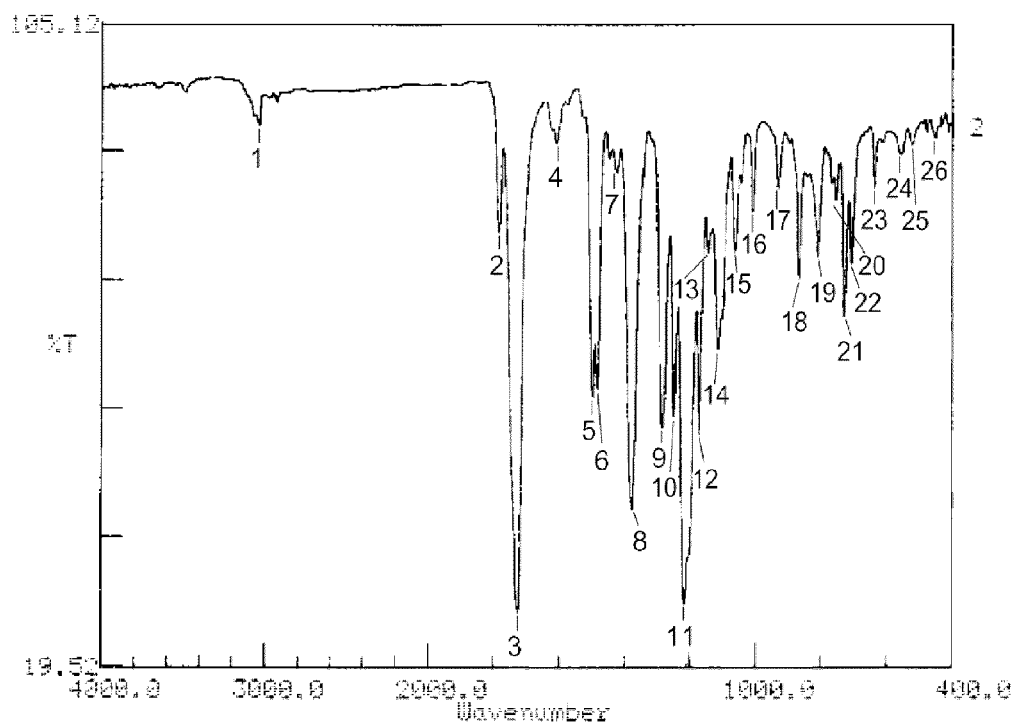

[Fig. 7]
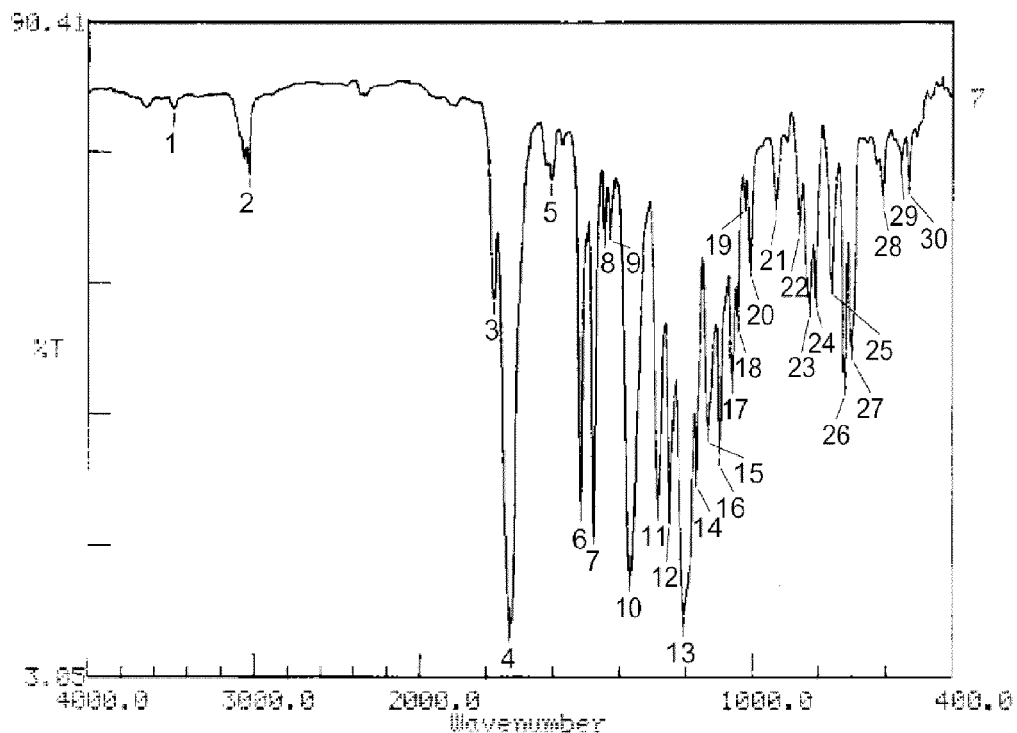

[Fig. 8]
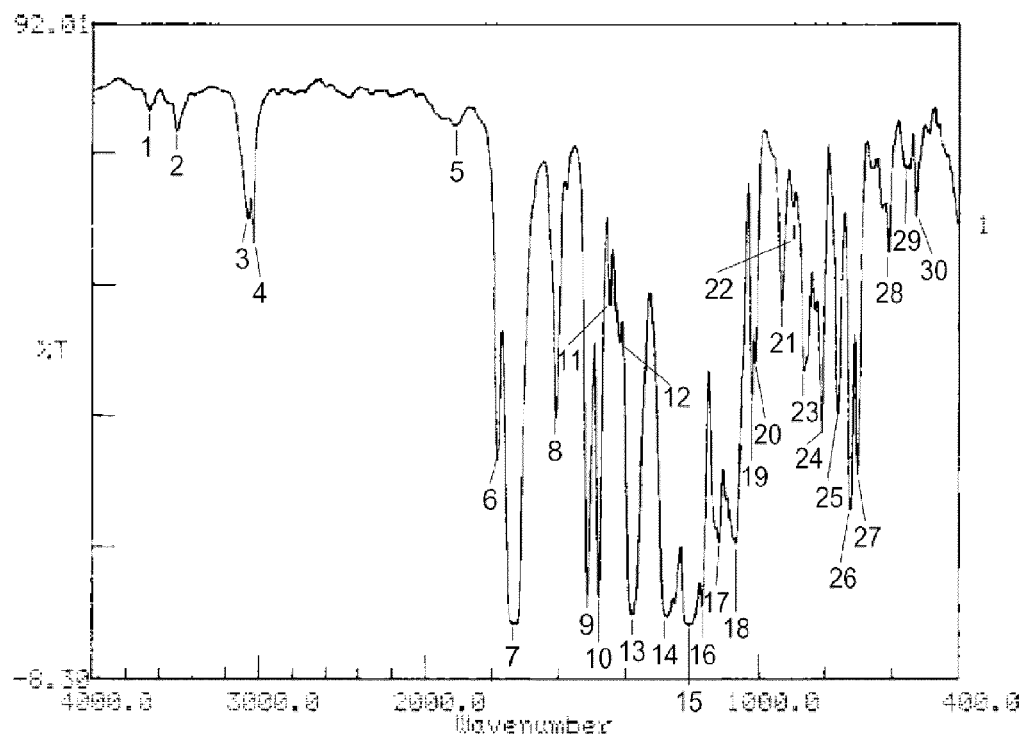

[Fig. 9]
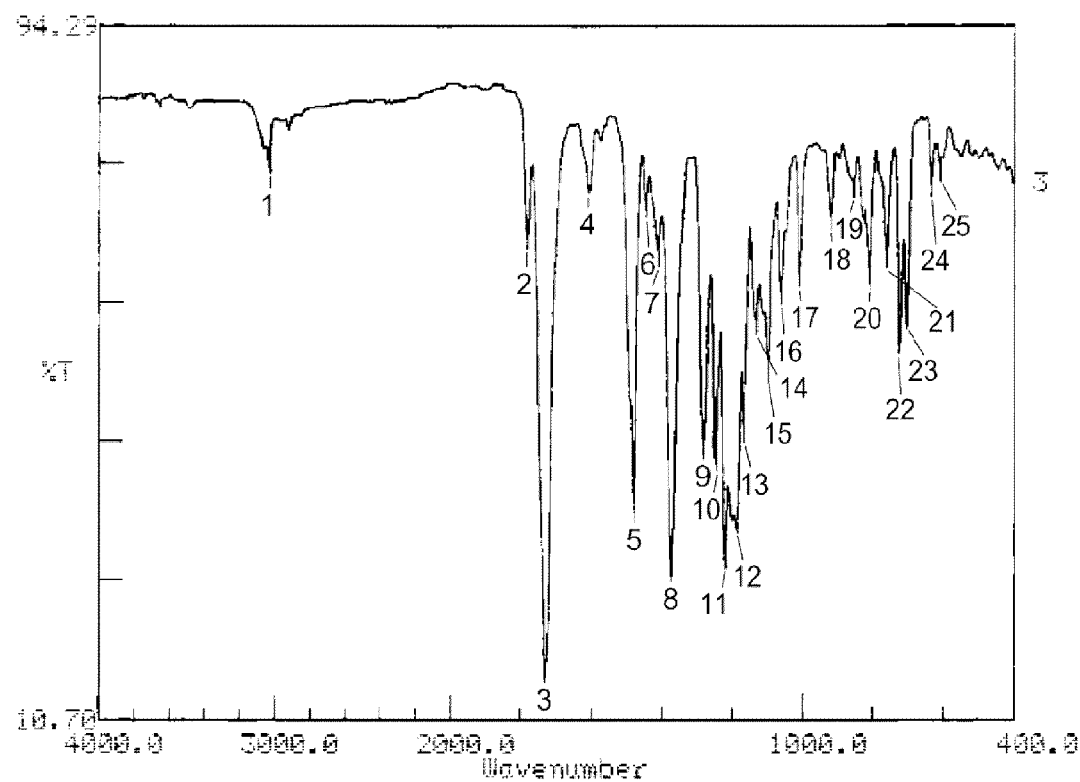

[Fig. 10]
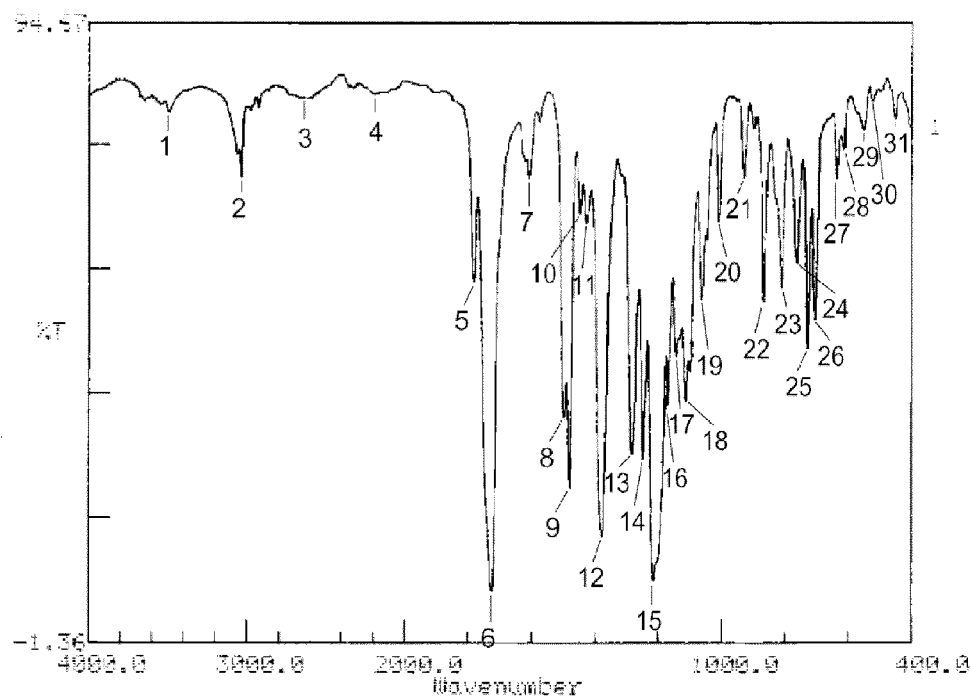

[Fig. 11]
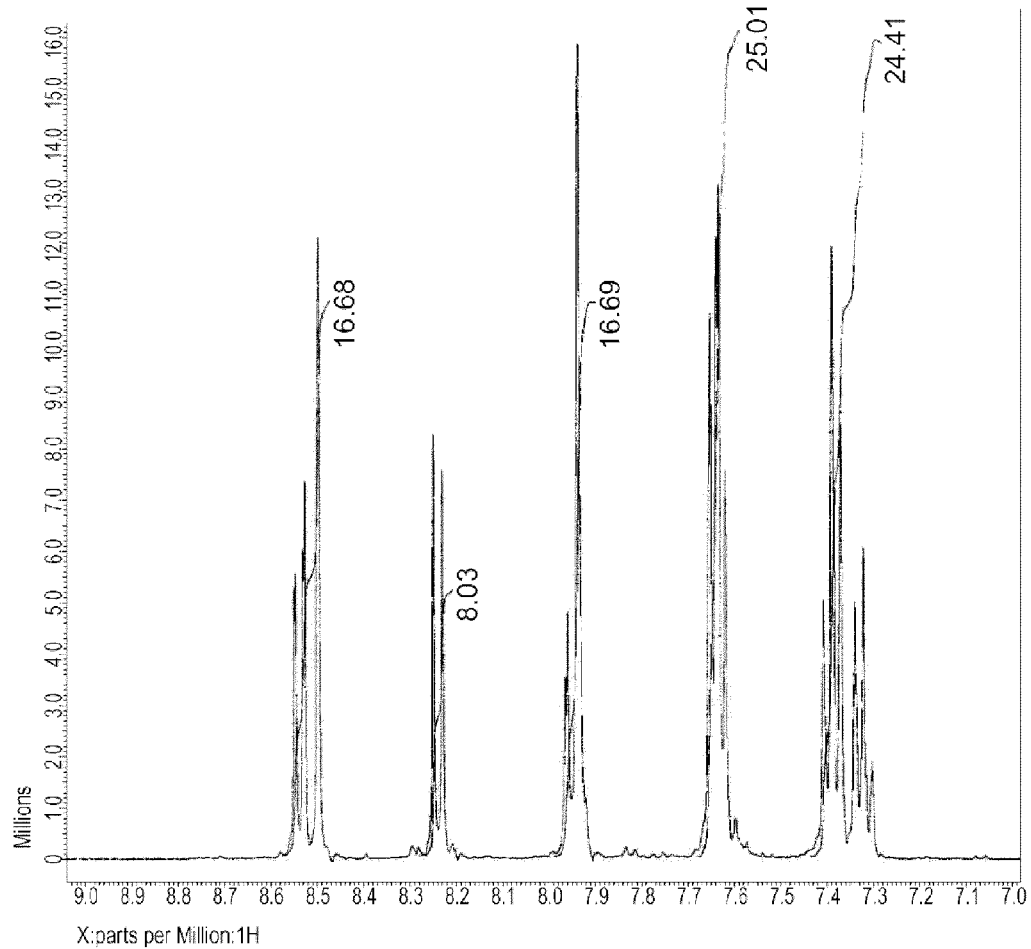

[Fig. 12]
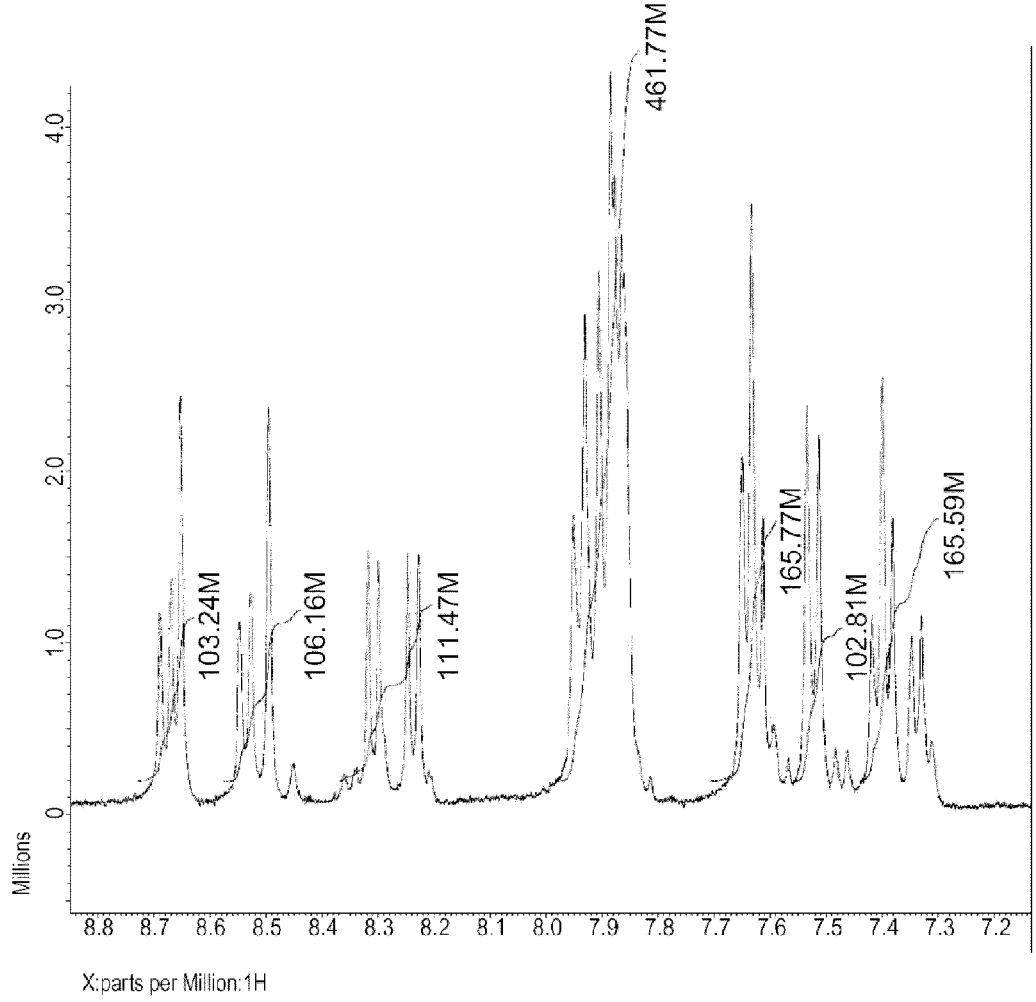

[Fig. 13]
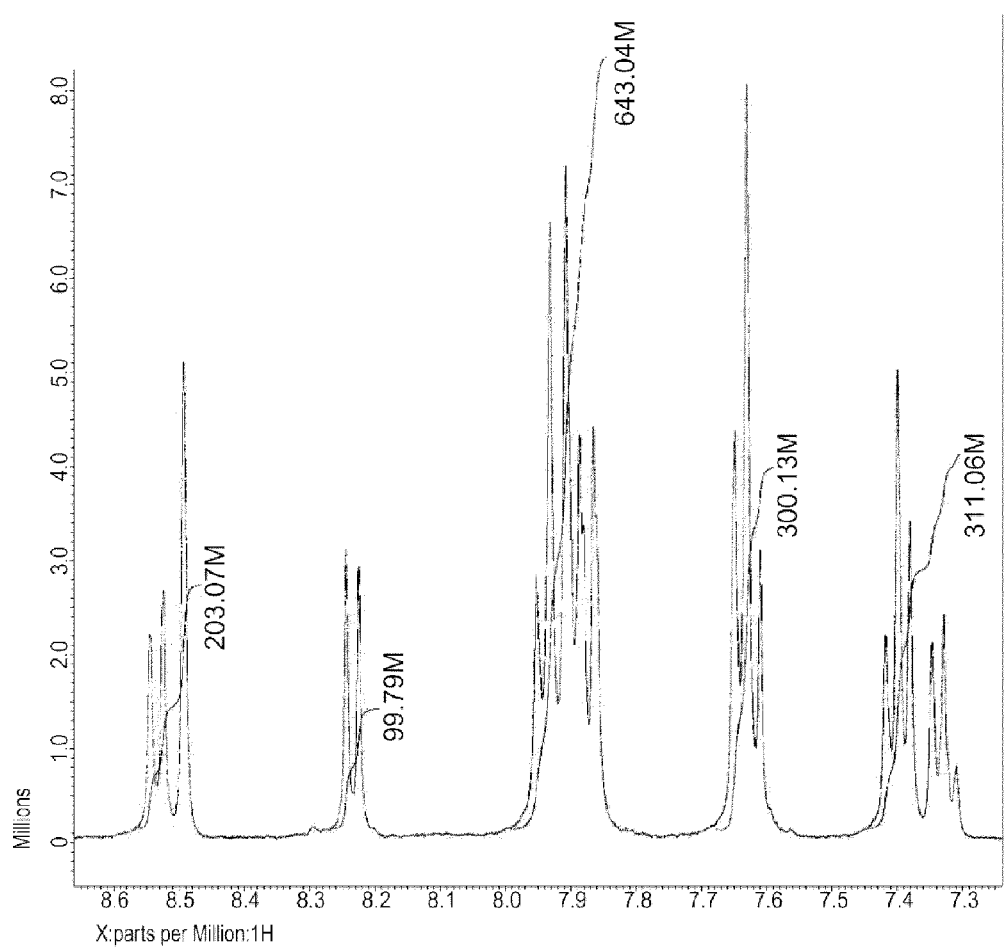

ESTER GROUP-CONTAINING TETRACARBOXYLIC ACID DIANHYDRIDE, POLYESTER POLYIMIDE PRECURSOR, POLYESTERIMIDE, AND METHODS FOR PRODUCING SAME

This application is the U.S. National Phase under 35 U.S.C §371 of International Application PCT/JP2010/052092, filed Feb. 12, 2010, which claims priority to Japanese Patent Application Nos. 2009-030494, filed Feb. 12, 2009 and 2009-156229, filed Jun. 30, 2009. The International Application was published under PCT Article 21(2) in a language other than English.

TECHNICAL FIELD

The present invention relates to a polyesterimide offering a high glass transition temperature, coefficient of linear thermal expansion equivalent to or lower than those of metal foils, extremely low coefficient of water absorption, extremely low coefficient of hygroscopic expansion, excellent flame resistance, relatively low elastic modulus and sufficient film toughness, and which is useful for flexible printed circuit (FPC) substrates, chip-on-film (COF) substrates and tape automation bonding (TAB) substrate materials, especially as FPC substrate materials (base film), and also provides the manufacturing methods thereof.

PRIOR ART

Due to not only its excellent heat resistance but also other properties such as chemical resistance, radiation resistance, electrical insulation property, excellent mechanical properties and the like, today polyimides are widely used in various electronic devices such as FPC, COF and TAB substrates, protection films for semiconductor elements, inter-layer insulation films for integrated circuits and the like. Importance of polyimides has been increasing in recent years because, in addition to offering the above characteristics, polyimides are easy to manufacture, have extremely high film purity and permit easy modification of their physical properties using various monomers that are readily available.

As electronic devices become increasingly lighter, thinner, shorter and smaller, the requirements on characteristics of polyimides also become tougher each year, and now the market is demanding multi-functional polyimide materials that not only offer solder heat resistance, but also, at the same time, demonstrate other multiple characteristics in film-forming such as dimensional stability against the heat cycle and moisture absorption; transparency; good bonding with metal layers; flame resistance; formability; and processability of fine shapes such as via holes.

Demand for polyimides for use in FPC, COF and TAB substrates has been increasing dramatically in recent years. Structures of these original fabric materials, or specifically copper-clad laminates (CCLs), are largely classified into three types. They are: 1) 3-layer type where polyimide film and copper foil are bonded together using an epoxy adhesive, etc.; 2) 2-layer type with no use of adhesive where a polyimide varnish is applied onto copper foil and then dried, or a polyimide precursor (polyamide acid) varnish is applied and then dried/imidized, or a copper layer is formed on polyimide film by means of deposition, sputtering, etc.; and 3) quasi-2-layer type where a thermoplastic polyimide is used as an adhesive layer. In applications where polyimide film must have high dimensional stability, 2-layer FCCLs that do not use adhesive are advantageous. Dimensional stability is required in terms of both heat expansion and hygroscopicity.

When used as an insulation material in a FPC substrate, for example, polyimide changes its dimension as it is exposed to various heat cycles in the mounting process. To minimize this dimensional change, it is desirable that the Tg of polyimide be higher than the process temperature and that the coefficient of linear thermal expansion of polyimide be as low as possible at a temperature of the Tg or lower. As explained later, controlling the coefficient of linear thermal expansion of the polyimide layer is extremely important in order to reduce the residual stress that generates in the 2-layer CCL manufacturing process.

Many polyimides are insoluble in organic solvents and do not melt at their glass transition temperature or higher, so it is normally not easy to form/process polyimides themselves. Accordingly, polyimide film is generally produced by causing an aromatic tetracarboxylic acid dianhydride such as pyromellitic anhydride (PMDA) or the like to undergo equimolar reaction with an aromatic diamine such as 4,4'-oxydianiline (ODA) or the like in an aprotic polar organic solvent such as dimethylacetamide (DMAc) or the like to produce a highly polymerized polyimide precursor (polyamide acid) first, and then applying varnish of the obtained precursor onto the copper foil and heating at 250 to 400° C. to achieve dehydrative ring-closure (imidization).

After the imidization reaction at high temperature, a residual stress generates when the polyimide/metal substrate laminate is cooled down to a room temperature, and this residual stress may sometimes cause serious problems to the CCL, such as warping, separation and broken film.

An effective method to reduce the heat stress is to cause the polyimide itself, which is an insulation film, to possess low heat expansion property. Most polyimides have a coefficient of linear thermal expansion in a range of 40 to 100 ppm/K, which is much higher than the coefficients of linear thermal expansion of metal foils, such as that of copper which is 17 ppm/K. Accordingly, R&D efforts are underway to develop polyimides having low heat expansion property closer to that of copper, or around 20 ppm/K or less.

The most well-known polyimide material having low heat expansion property that is currently used in practical applications is the polyimide formed from 3,3',4,4'-biphenyltetracarboxylic acid dianhydride and p-phenylenediamine. This polyimide film is known to exhibit a very low coefficient of linear thermal expansion of 5 to 15 ppm/K, although the specific value of the coefficient varies depending on the film thickness and film-forming conditions (refer to Non-patent Literature 1, for example). However, a problematic feature that has been pointed out is that this polyimide film has a high coefficient of water absorption.

Dimensional stability required of polyimides relates not only to heat cycles, but also to moisture absorption. Conventional polyimides absorb as much as 2 to 3 percent by weight of moisture. In high-density wirings and multi-layer wirings, moisture absorption by insulation layers can cause the problems of a drop in electrical properties such as shifted circuit positions due to dimensional change, corrosion or ion migration at polyimide/conductor interface, dielectric breakdown, or the like. Therefore, suppression of moisture absorption has been an extremely important issue to be improved. For this reason, polyimide layers must have as low a coefficient of water absorption as possible.

As one example of molecular design aimed at lowering the coefficient of water absorption of polyimide, it has been reported that using an ester group-containing tetracarboxylic acid dianhydride expressed by Formula (4) below to introduce an ester bonding to the polyimide skeleton is effective (refer to Non-patent Literature 2, for example):

[Chemical 4]

(4)

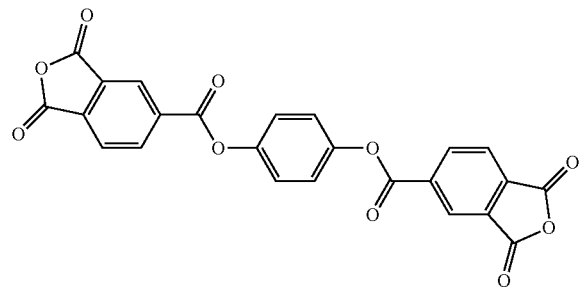

In addition to the above, several polyimides, all obtained from an ester group-containing tetracarboxylic acid dianhydride and each having a different structure, have been reported (refer to Patent Literatures 1 to 6, for example).

Assume an ester group-containing tetracarboxylic acid dianhydride expressed by Formula (5), for example, which is the same as Formula (4) above but introducing the p-polyphenylene group instead of the phenylene group at the center:

[Chemical 5]

(5)

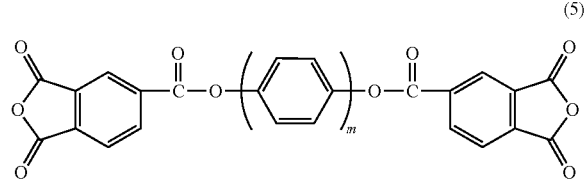

As this ester group-containing tetracarboxylic acid dianhydride offers a greater number of p-phenylene groups such as the p-biphenylene group (m=2 in Formula (5)) (refer to Patent Literature 4, for example), p-terphenylene group (m=3) and p-quarterphenylene group (m=4), it is expected to enable a reduction of the coefficient of water absorption and coefficient of hygroscopic expansion of the obtained polyimide film while keeping its low heat expansion characteristics.

However, an introduction of p-polyphenylene groups such as p-biphenylene group and the like makes the molecular structure extremely rigid, which inevitably leads to a significant drop in solvent solubility. In other words, since these monomers are not easy to dissolve in the polymerization solvent at the time of polymerization reaction, they remain undissolved even after the polymerization reaction, thereby creating a need to filter the varnish using a glass filter, etc., or agitate the mixture for an extremely long period of time, or they present serious problems in the manufacturing process, such as gelling of the polymerization solution.

It is expected that introducing substituents such as alkyl groups or alkoxy groups or the like to the p-polyphenylene group in Formula (5) above will improve the solvent solubility of monomers (refer to Patent Literature 6, for example). However, polyimide film obtained from a tetracarboxylic dianhydride to which these aliphatic substitution groups only have been introduced does not necessarily offer sufficient physical properties, and further improvements are needed. On the other hand, the introduction of halogen substitution groups, one representative example of which is the Cl group, can improve solvent solubility of monomers and flame resistance of polyimide film at the same time. However, an introduction of halogen substitution groups is not feasible because the resulting polyimide film will generate greater environmental burdens when it is disposed of.

In the fields of FPC, TAB and COF to which the polyimide film proposed by the present invention is applied, FPC applications are seeing that the reduction of elastic modulus has become an important challenge in recent years because the elastic modulus of those conventional polyimide films with low heat expansion property is too high. This is because if a FPC must be bent rapidly at a small radius of curvature to be mounted in a small space, problems such as separation at the copper foil/polyimide interface are likely to occur if the repulsive force that generates when the FPC is bent is high, resulting in a significant loss of electrical reliability at the bent location. An effective way to avoid these problems is to reduce the thickness of both the copper foil and heat-resistant insulation layer (base film), while lowering the elastic modulus of the polyimide film constituting the base film. However, a molecular design where a rigid, highly linear skeletal structure is selected to achieve high in-plane orientation of the polyimide chain, solely for the purpose to achieve a low CTE value close to that of copper foil as required of the base film, would increase the elastic modulus of the polyimide film. Accordingly, it is not easy to achieve low CTE and low elastic modulus at the same time.

It is not easy to obtain a FPC base film material that retains solvent solubility of monomers, polymerization reactivity of polyimide precursor based thereon (productivity), varnish uniformity, and storage stability, while satisfying all of the following characteristics of polyimide film: Low coefficient of linear thermal expansion (target value: 20 ppm/K or less), low coefficient of water absorption (target value: 0.5% or less), low coefficient of hygroscopic expansion (target value: 10 ppm/RH % or less), sufficient film toughness (target value: breaking elongation>20%), solder heat resistance (target value: Tg>300° C.), flame resistance (target value: V-0 level per UL94 standard), and substantially lower modulus of tensile elasticity compared to conventional base film materials (target value: 4 GPa or less). No practical heat-resistant insulation material that meets the above required characteristics at the same time has been known.

Patent Literature 1: Japanese Patent Laid-open No. Hei 10-070157
Patent Literature 2: Japanese Patent Laid-open No. Hei 11-263785
Patent Literature 3: Japanese Patent Laid-open No. 2005-298623
Patent Literature 4: Japanese Patent Laid-open No. 2006-013419
Patent Literature 5: Japanese Patent Laid-open No. Hei 09-258229
Patent Literature 6: International Patent Laid-open No. 2008/091011, Brochure
Non-patent Literature 1: Macromolecules, 29, 7897 (1996)
Non-patent Literature 2: High Performance Polymers, 18, 697 (2006)

SUMMARY OF THE INVENTION

Problems to Be Solved by the Invention

The object of the present invention is to provide a polyesterimide which simultaneously offers high glass transition temperature, low coefficient of linear thermal expansion equivalent to or lower than those of metal foils, extremely low coefficient of water absorption, extremely low coefficient of hygroscopic expansion, excellent flame resistance, relatively low elastic modulus and sufficient film toughness, and which is useful for FPC substrates, COF substrates and TAB substrate materials, especially as FPC substrate materials (base film), as well as to provide the manufacturing methods thereof.

Means for Solving the Problems

After repeatedly conducting earnest studies to achieve the aforementioned object, the inventors found that a polyesterimide made from an ester group-containing tetracarboxylic acid dianhydride characterized by its skeletal structure having a bulky phenyl substitution groups while maintaining a rigid, linear skeletal structure, by causing it to react against diamine under polymerization reaction and then imidizing the obtained polyesterimide precursor, not only offers better results than do conventional polyesterimides for a majority or some of the various physical properties mentioned in the aforementioned description or the object, but it also meets all or most of the target physical properties mentioned in the aforementioned description, and consequently completed the present invention.

In other words, according to the present invention, the ester group-containing tetracarboxylic acid dianhydride proposed by the present invention is an ester group-containing tetracarboxylic acid dianhydride expressed by General Formula (1):

[Chemical 1]

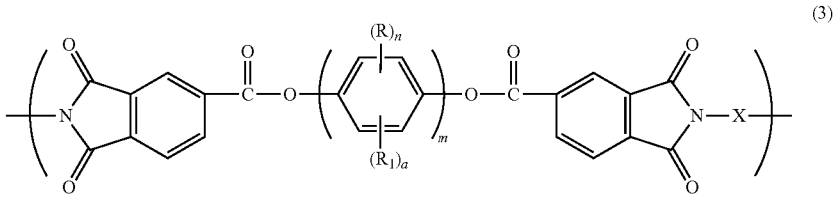

(1)

(In the formula, R represents a phenyl group, $R_1$ represents an alkyl group with 1 to 6 carbon atoms or alkoxy group with 1 to 6 carbon atoms, n each independently takes a value of 0 to 4, a each independently takes a value of 0 to 4, and m represents an integer of 2 to 4; where not all n's are 0 at the same time and $0 \leq n+a \leq 4$ is satisfied by each phenylene group.)

Also, the polyester imide precursor proposed by the present invention, obtained by reacting the aforementioned dianhydride and amine, is a polyesterimide precursor having a repeating unit expressed by General Formula (2):

[Chemical 2]

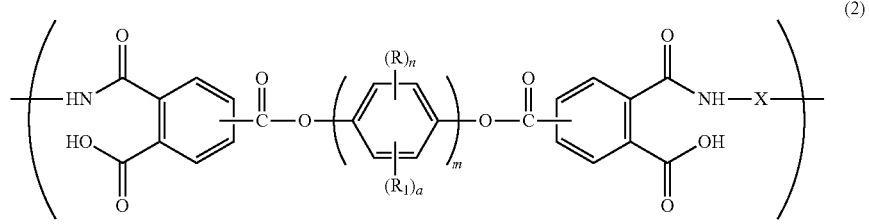

(In the formula, R, $R_1$, n, m and a are the same as the corresponding items in General Formula (1), while X represents a divalent aromatic group and/or aliphatic group and the ester group is bonded at the meta- or para-position relative to the amide bond.)

As for the bonding position of the ester group, the m-position relative to the amide bond only corresponds to the p-position relative to the carboxyl group.

Additionally, the aforementioned polyesterimide precursor having a intrinsic viscosity of 0.1 to 20.0 dL/g is a favorable embodiment of the present invention.

Furthermore, the polyesterimide of the present invention obtained from such polyesterimide precursor is a polyesterimide having a repeating unit expressed by General Formula (3):

[Chemical 3]

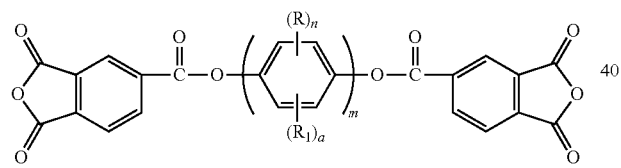

(3)

(In the formula, R, $R_1$, n, m, a and X are the same as the corresponding items in General Formula (2).)

The present invention also provides a manufacturing method of the polyesterimide expressed by General Formula (3), which is produced by causing the polyesterimide precursor expressed by General Formula (2) above to undergo imidization reaction by means of heating or using a cyclodehydration reagent.

Effects of the Invention

The present invention provides a polyesterimide film extremely useful in industrial application, by using the ester group-containing tetracarboxylic acid dianhydride expressed by Formula (1) as the material and combining it with various diamines to undergo a polymerization reaction, after which a varnish of the obtained polyesterimide precursor is applied on a substrate of metal foil, etc., and then dried/imidized.

Due to the characteristics of the aforementioned ester group-containing tetracarboxylic acid dianhydride due to its molecular structure, or specifically the rigidity and three-dimensional bulkiness of substituents, the polyesterimide proposed by the present invention exhibits excellent solvent solubility and high polymerization reaction property at the time of polymerization reaction, and in its film form this polyesterimide offers excellent physical properties such as low coefficient of linear thermal expansion, low coefficient of water absorption, low coefficient of hygroscopic expansion, high glass transition temperature, low elastic modulus and/or film toughness and the like, where a majority or some of these physical properties are better than those of conventional polyesterimide films. Therefore, it is possible to obtain a heat-resistant insulation material not heretofore achievable with conventional materials that preferably provides coefficient of linear thermal expansion equivalent to or lower than those of metal foils, extremely low coefficient of water absorption, extremely low coefficient of hygroscopic expansion, high glass transition temperature, excellent flame resistance, relatively low elastic modulus and sufficient film toughness, more preferably demonstrating at the same time other physical properties such as excellent bonding strength with metal such as copper foil and the like. Accordingly, the polyesterimide proposed by the present invention is extremely useful for FPC substrates, COF substrates and TAB substrate materials, especially as FPC substrate materials (base film).

BRIEF DESCRIPTION OF THE DRAWINGS

FIG. 1 shows the infrared absorption spectrum of a polyesterimide thin film. (Example 4)

FIG. 2 shows the infrared absorption spectrum of a polyesterimide thin film. (Example 5)

FIG. 3 shows the infrared absorption spectrum of a polyesterimide thin film. (Example 6)

FIG. 4 shows the infrared absorption spectrum of a polyesterimide thin film. (Example 7)

FIG. 5 shows the infrared absorption spectrum of a polyesterimide thin film. (Example 8)

FIG. 6 shows the infrared absorption spectrum of a polyesterimide thin film. (Example 9)

FIG. 7 shows the infrared absorption spectrum of a polyesterimide thin film. (Example 10)

FIG. 8 shows the infrared absorption spectrum of a polyesterimide thin film. (Example 11)

FIG. 9 shows the infrared absorption spectrum of a polyesterimide thin film. (Example 12)

FIG. 10 shows the infrared absorption spectrum of a polyesterimide thin film. (Example 13)

FIG. 11 shows the $^1$H-NMR spectrum of an ester group-containing tetracarboxylic acid dianhydride. (Example 1)

FIG. 12 shows the $^1$H-NMR spectrum of an ester group-containing tetracarboxylic acid dianhydride. (Example 2)

FIG. 13 shows the $^1$H-NMR spectrum of an ester group-containing tetracarboxylic acid dianhydride. (Example 3)

MODE FOR CARRYING OUT THE INVENTION

A mode for carrying out the present invention is explained below in detail.

The new ester group-containing tetracarboxylic acid dianhydride proposed by the present invention, which can be used as a material for the polyesterimide conforming to the present invention, is expressed by General Formula (1) below:

[Chemical 1]

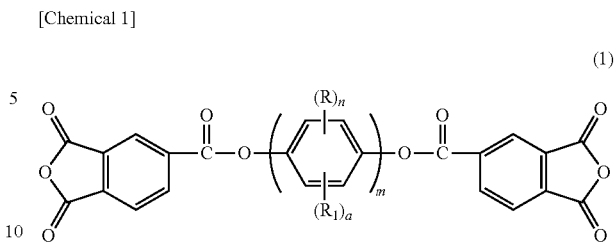

In the formula, R represents a phenyl group, $R_1$ represents an alkyl group with 1 to 6 carbon atoms or alkoxy group with 1 to 6 carbon atoms, n each independently takes a value of 0 to 4, a each independently takes a value of 0 to 4, and m represents an integer of 2 to 4; where not all n's are 0 at the same time and $0 \le n+a \le 4$ is satisfied by each phenylene group.

One characteristic of this ester group-containing tetracarboxylic acid dianhydride proposed by the present invention is that a p-polyphenylene group is introduced to the structure via a phenyl substitution group-containing para-ester bonding. By using such monomer, a polyimide having bulky phenyl substitution groups while maintaining a rigid, linear main chain structure can be obtained.

Accordingly in General Formula (1), R represents a phenyl group and n each independently takes a value of 0 to 4. n is preferably 0, 1 or 2, and more preferably 0 or 1. However, the phenyl group must have at least one substitution on the p-polyphenylene structure at the center of the molecule. In other words, not all n's are 0 at the same time. The number of R substitutions in the entire p-polyphenylene group is preferably 1 to 4, or more preferably 1 or 2, where, if there are two or more R substitutions in the entire p-polyphenylene group, it is more preferable that the number of R substitutions in the entire p-polyphenylene group be m or less and that n in each phenylene group be 0 or 1. Also, an alkyl group or alkoxy group illustrated by R1 below may be substituted to the phenyl group R to the extent that the effects of the present application for patent are not lost, where, if the phenyl group R has a substituent, the substituent is preferably an alkyl group, or more preferably an alkyl group with 1 to 4 carbon atoms, or most preferably a methyl group. The number of such substituent is preferably 1 or 2. However, it is desirable for the phenyl group R to have no substituent to ensure flame resistance.

Also, m is an integer of 2 to 4 and in a p-polyphenylene structure of m=3 or greater, it is preferable that a phenyl group be substituted to the phenylene nucleus at the end.

Also, $R_1$ is an alkyl group with 1 to 6 carbon atoms or alkoxy group with 1 to 6 carbon atoms, where it is preferably an alkyl group with a carbon atom number of 1 to 6. The alkyl group with 1 to 6 carbon atoms may be a straight-chain or branched-chain alkyl group, or cycloalkyl group having a cyclic structure. It is preferably a straight-chain or branched-chain alkyl group with 1 to 4 carbon atoms or cycloalkyl group with 5 or 6 carbon atoms. Specific examples include methyl group, ethyl group, isopropyl group, n-propyl group, sec-butyl group, t-butyl group, cyclohexyl group, etc., among which methyl group is most preferable.

On the other hand, the alkoxy group with 1 to 6 carbon atoms may be a straight-chain or branched-chain alkoxy group, or cycloalkoxy group having a cyclic structure. It is preferably a straight-chain or branched-chain alkoxy group with 1 to 4 carbon atoms or cycloalkoxy group with 5 or 6 carbon atoms. Specific examples include methoxy group, ethoxy group, isopropyloxy group, cyclohexyloxy group, and the like. Additionally, a each independently takes a value of 0 to 4, or preferably 0, 1, or 2, and more preferably 0 or 1. Desirably a each should be 0 or 1 in all phenylene groups to ensure flame resistance, and more preferably 0. If a is 1, $R_1$ is preferably an alkyl group, or more preferably a group having less carbon atoms such as a methyl group or the like. Also, the sum of n and a in each phenylene group meets 0≤n+a≤4. If two or more $R_1$ are substituted to the p-polyphenylene group, $R_1$s may be the same or different.

From the viewpoints of ease of synthesis, availability of materials, material costs, and so on, specific examples of the ester group-containing tetracarboxylic acid dianhydride expressed by General Formula (1) above include the ester group-containing tetracarboxylic acid dianhydrides expressed by Formulae (6) to (8) below:

[Chemical 6]

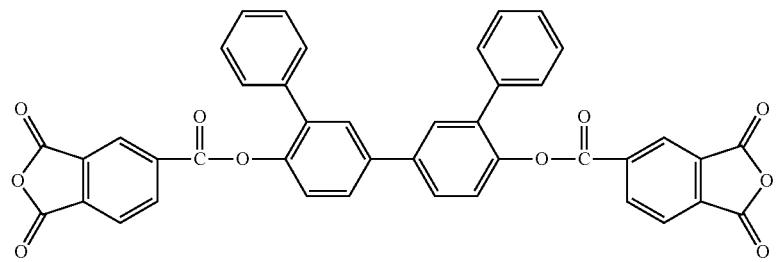

(6)

[Chemical 7]

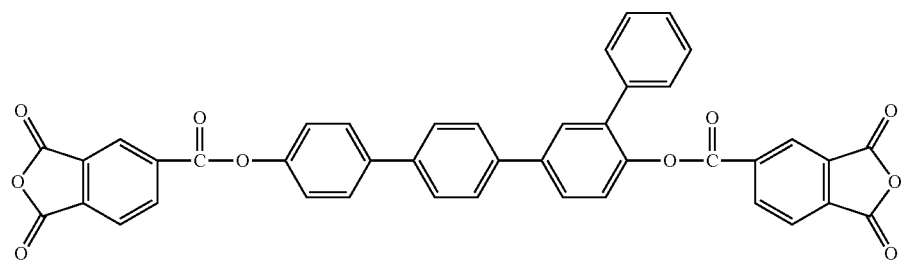

(7)

[Chemical 8]

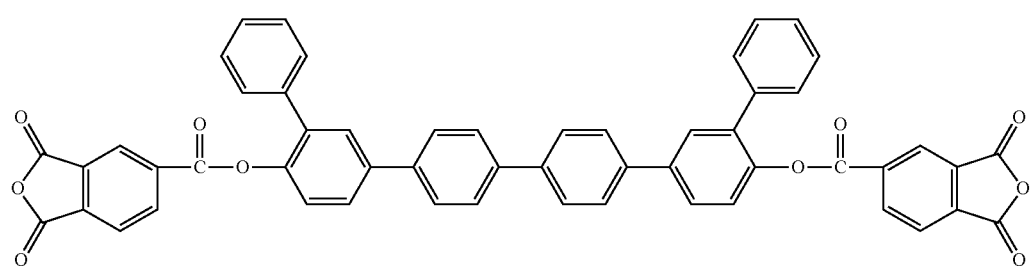

(8)

Other examples include the following ester group-containing tetracarboxylic acid dianhydrides: 4,4'-bis(1,3-dioxo-1,3-dihydroisobenzofuran-5-ylcarbonyloxy)-3,3'-dimethyl-5,5'-diphenylbiphenyl, 4,4'-bis(1,3-dioxo-1,3-dihydroisobenzofuran-5-ylcarbonyloxy)-3,3'-di-t-butyl-5,5'-diphenylbiphenyl, 4,4'-bis(1,3-dioxo-1,3-dihydroisobenzofuran-5-ylcarbonyloxy)-3,3'-dimethoxy-5,5'-diphenylbiphenyl, 4,4''-bis(1,3-dioxo-1,3-dihydroisobenzofuran-5-ylcarbonyloxy)-3-methyl-5-phenyl-p-terphenyl, 4,4''-bis(1,3-dioxo-1,3-dihydroisobenzofuran-5-ylcarbonyloxy)-3,3''',5,5'''-tetraphenyl-p-quarterphenyl, or the like.

The manufacturing method of the ester group-containing tetracarboxylic acid dianhydride proposed by the present invention and expressed by General Formula (1), is not specifically limited and, for example, said ester group-containing tetracarboxylic acid dianhydride can be synthesized via esterification reaction of a dihydroxy-p-polyphenylene compound having a phenyl substitution group expressed by General Formula (9) below (hereinafter also referred to as "Diol") or derivative thereof, with trimellitic anhydride or derivative thereof:

[Chemical 9]

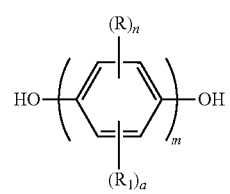

(9)

(In the formula, R, $R_1$, n, m and a are the same as the corresponding items in General Formula (1).)

Also, the dihydroxy-p-polyphenylene compound expressed by General Formula (9) above forms the skeletal structure of the polyesterimide proposed by the present invention, where specific examples include:

3-phenyl-4,4'-dihydroxybiphenyl, 3,3'-diphenyl-4,4'-dihydroxybiphenyl

[Chemical 10]

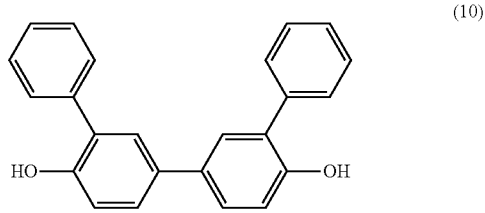

(10)

3-phenyl-4,4"-dihydroxy-p-terphenyl

[Chemical 11]

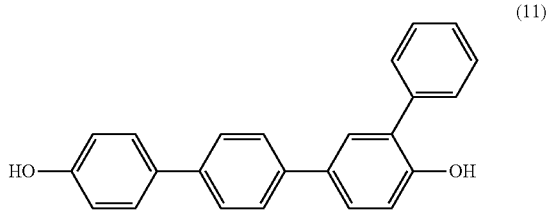

(11)

3,3"-diphenyl-4,4"-dihydroxy-p-terphenyl, 3,3'''-diphenyl-4,4'''-dihydroxy-p-quarterphenyl

[Chemical 12]

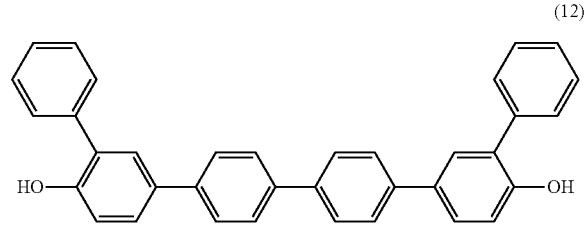

(12)

3,3'-dimethyl-4,4'-dihydroxy-5,5'-diphenylbiphenyl, 3,3'-di-t-butyl-4,4'-dihydroxy-5,5'-diphenylbiphenyl, 3,3'-dimethoxy-4,4'-dihydroxy-5,5'-diphenylbiphenyl, 4,4"-dihydroxy-3-methyl-5-phenyl-p-terphenyl, 4,4'''-dihydroxy-3,3''',5,5'''-tetraphenyl-p-quarterphenyl, and the like.

The diol expressed by General Formula (9) above can be synthesized by any known manufacturing method.

For example, it can be obtained by causing an alkoxybenzene having a bromine group substituted to its phenyl group, to react with an alkoxybenzene whose phenyl group has a bromomagnesium group, and then dissociating the alkyl group from the alkoxyl group of the obtained product by means of BBr3 or HBr to form a hydroxy group, as described in Japanese Patent Laid-open No. Hei 2-212449 or the like.

Also in the case of m=2 (biphenylene) in General Formula (9) above, the aforementioned diol can be obtained by oxidative-coupling a phenyl-substituted t-butylphenol and then reducing it to obtain a biphenol, followed by dissociation of t-butyl, as described in NL 6410238 Laid-open. Or, it can also be obtained by causing phenyl phenols whose phenyl group has a halogen group, to react with each other, as described in Japanese Patent Laid-open No. Hei 8-27051 or Japanese Patent Laid-open No. Sho 56-53631.

If m=3 (terphenylene) or 4 (quarterphenylene), the aforementioned diol can also be obtained by causing 4-(4-hydroxyphenyl)cyclohexanone or 4,4'-bicyclohexanone to react with a phenol in the presence of an acid catalyst and then thermally breaking down the obtained bisphenol, followed by dehydrogenation of the obtained reaction product, as described in Japanese Patent Laid-open No. 2002-234856 or Japanese Patent Laid-open No. 2005-247809.

The manufacturing method of ester group-containing tetracarboxylic acid dianhydride by esterification reaction from the above diol or derivative thereof and trimellitic anhydride or derivative thereof, is not specifically limited and any known method can be applied. For example, a method wherein the hydroxy group of the diol expressed by General Formula (9) and carboxyl group of trimellitic anhydride can be put through direct dehydration reaction at high temperature, or a dehydration reagent such as dicyclohexylcarbodiimide or the like may be used to achieve dehydration condensation; a method wherein diol diacetate and trimellitic anhydride can be reacted with each other at high temperature, followed by removal of acetic acid and esterification (ester exchange method); a method wherein carboxyl group of trimellitic anhydride can be converted to acid halide, which is then reacted with diol in the presence of a deoxidizer (base) (acid halide method); a method wherein tosyl chloride/N,N-dimethylformamide/pyridine mixture can be used to activate the carboxyl group in trimellitic anhydride in order to achieve esterification, or the like can be listed. Among the above methods, the ester exchange method and the acid halide method can be applied favorably in terms of economy and reactivity.

As an example of a favorable method, the method to synthesize the ester group-containing tetracarboxylic acid dianhydride proposed by the present invention by means of esterification reaction based on the acid halide method is explained below in greater detail. First, a trimellitic anhydride chloride is dissolved in a solvent and the container is sealed with a septum cap. Next, a solution prepared by dissolving a diol expressed by General Formula (9) and appropriate amount of base (deoxidizer) in the same solvent, is dropped into the first solution using a syringe or drip funnel. When the dropping of the solution is complete, the reaction mixture is agitated for one to 24 hours. At this time, normally the amount of trimellitic anhydride chloride added is twice that of diol in mols (chemical equivalent). However, a large amount of trimellitic anhydride chloride may be added to diol in the above reaction, because trimellitic anhydride chloride has far better solvent solubility than diol and it can easily be dissolved and removed through solvent wash after the reaction. An applicable amount of trimellitic anhydride chloride to be added is 2 to 10 times in mols, or preferably 2 to 5 times in mols, the amount of diol.

Solvents that can be used in the above esterification reaction are not specifically limited, but examples include aprotic solvents such as tetrahydrofuran (hereinafter referred to as "THF"), 1,4-dioxane, picoline, pyridine, acetone, chloroform, toluene, xylene, dichloromethane, 1,2-dichloroethane, N-methyl-2-pyrrolidone, N,N-dimethylacetamide (hereinafter referred to as "DMAc"), N,N-diethylacetamide, N,N-dimethylformamide (hereinafter referred to as "DMF"), hexamethyl phosphoramide, dimethylsulfoxide, γ-butyrolactone, 1,3-dimethyl-2-imidazolidinone, 1,2-dimethoxyethane-bis (2-methoxyethyl)ether and the like; and protic solvents such as phenol, o-cresol, m-cresol, p-cresol, o-chlorophenol, m-chlorophenol, p-chlorophenol and the like. These solvents can be used alone or two or more of them can be mixed together. Among others, THF, DMF and DMAc can be used favorably from the viewpoint of material solubility. Also, it is desirable that these solvents be dehydrated by adding molecular sieves or the like.

The above esterification reaction is implemented at −10 to 50° C., or preferably at 0 to 30° C. The reaction temperatures above 50° C. are not desirable because such high temperatures may partially cause side reaction to lower the yield.

The reaction to obtain said ester group-containing tetracarboxylic acid dianhydride is implemented at solute concentrations in a range of 1 to 50 percent by weight. When the control of side reaction and the precipitate filtration process are considered, a preferable range of solute concentrations is 5 to 30 percent by weight.

The deoxidizer used in the reaction is not specifically limited, and organic tertiary amines such as pyridine, triethylamine, N,N-dimethylaniline and the like, epoxies such as propylene oxide and the like, or inorganic bases such as potassiumcarbonate, sodiumhydroxide and the like can be used. Among others, pyridine can be used favorably from the viewpoints of separation after reaction, cost, toxicity, etc.

The said obtained ester group-containing tetracarboxylic acid dianhydride is separated/refined as follows. To be specific, an example of using pyridine as the deoxidizer is explained. If the solubility of the target substance in the solvent used is high after the above esterification reaction is complete, filter out the produced pyridine hydrochloride from the reaction mixture, and then the filtrate is solvent-distilled using an evaporator to obtain precipitates. If excessive trimellitic anhydride chloride was used in the esterification reaction, the aforementioned precipitates are washed first using a non-polar solvent such as cyclohexane, toluene or the like, and then residual trimellitic anhydride chloride is dissolved/removed. This is followed by repeated washing with water to dissolve/remove the hydrochloride and the excessive pyridine, which is then followed by 24 hours of vacuum-drying at 100 to 230° C., to obtain a crude product in powder form. If the solubility of the target substance is low, however, the mixture of the precipitated target substance and pyridine hydrochloride are separated from the reaction solution via filtering, and if excessive trimellitic anhydride chloride was used earlier, precipitates are washed first using a non-polar solvent such as cyclohexane, toluene or the like, and then residual trimellitic anhydride chloride is dissolved/removed, followed by repeated washing with water to dissolve/remove the hydrochloride and the excessive pyridine. To remove pyridine hydrochloride and pyridine, it is also possible to condense the reaction solution using an evaporator to an appropriate degree, and then drip the condensed solution into a large amount of water to implement water washing and precipitation at the same time.

During the aforementioned water washing operation, whether the hydrochloride has been completely removed or not can be judged simply by checking if white precipitates of silver chloride form after dripping 1% aqueous nitric silver solution into the washing solution.

Also note that the aforementioned washing may cause acid anhydride groups in the ester group-containing tetracarboxylic acid dianhydride to partly hydrolyze and change to dicarboxylic acid. However, such dicarboxylic acid can be easily returned to acid anhydride groups by vacuum-drying at 100 to 250° C., or preferably at 120 to 200° C., to cause dehydrative ring-closure. It is also possible to use treatment with an organic acid anhydride instead of heating as described above. Organic acid anhydrides that can be used for this purpose include acetic anhydride, propionic anhydride, maleic anhydride, phthalic anhydride and the like, but acetic anhydride can be used favorably from the viewpoint of ease of removal. Thus, the obtained crude product is recrystallized using an appropriate solvent that does not react with the product, and then washed, heated and vacuum-dried to obtain the highly pure ester group-containing tetracarboxylic acid dianhydride under the present invention that can be used for polymerization.

Another example of a favorable method is explained, where the ester exchange method is used to cause esterification reaction in order to synthesize the ester group-containing tetracarboxylic acid dianhydride proposed by the present invention.

Under the ester exchange method, first a diol conforming to General Formula (9) above is turned into carboxylic acid diester. For example, a large amount of a carboxylic acid anhydride such as acetic anhydride or the like can be used to form a carboxylic acid ester of acetic acid, etc., or any phenol carboxylic acid ester manufacturing method, such as one reacting carboxylic acid or halogenated acyl in the presence of an esterified catalyst such as sulfuric acid, p-toluenesulfonic acid or the like, can be used to synthesize the ester group-containing tetracarboxylic acid dianhydride proposed by the present invention via ester exchange reaction of carboxylic acid diester, such as acetic acid diester, for example, with trimellitic anhydride. The amount of trimellitic anhydride used is preferably in a range of 2 to 10 times in mols, or more preferably 2.6 to 3.4 times in mols, the amount of acetic acid diester of diol.

The reaction temperature is preferably in a range of 200 to 230° C. A preferred catalyst is carboxylic acid lithium salt, such as lithium acetate. The amount of catalyst used is preferably in a range of 0.1 to 6 percent by mol relative to acetic acid diester of diol. Also, the reaction solvent may be an aromatic hydrocarbon having a high boiling point such as diphenyl ether or the like, where the amount of reaction solvent used is preferably 2 to 10 parts by weight relative to 1 part by weight of acetic acid diester of diol. Reaction can be implemented by putting material acetic acid diester and trimellitic anhydride, lithium acetate, and solvent in the reaction container and mixing them in an inert atmosphere under rising temperature, with the produced acetic acid distilled as the reaction progresses. When the reaction is complete, the target substance can be separated/refined from the reaction solution according to any known method, such as cooling the reaction liquid directly or adding a poor solvent to the reaction liquid and then cooling the mixture, followed by filtering out the precipitated crystal, and thereby a crude or highly pure form of the target substance can be obtained. If necessary, the obtained target substance can be recrystallized/filtered to obtain a product of higher purity.

For example, the solvent in which the target substance is dissolved can be filtered to separate inorganic salt, or washed with water, prior to crystallization in the above refining operation, to obtain a highly pure product containing even less metals such as inorganic salt.

Next, the manufacturing method of the polyesterimide precursor proposed by the present invention and expressed by General Formula (2) above is not specifically limited and any known method can be used. Specifically, the polyesterimide precursor can be obtained by the method explained below. First, diamine is dissolved in polymerization solvent, to which powder of the ester group-containing tetracarboxylic acid dianhydride proposed by the present invention and obtained by the aforementioned method is added gradually, followed by 0.5 to 100 hours, or preferably 1 to 48 hours, of agitation using a mechanical stirrer at 0 to 100° C., or preferably 20 to 60° C. At this time, the monomer concentration is 5 to 50 percent by weight, or preferably 10 to 40 percent by weight. When polymerization occurs in this monomer concentration range, a uniform, highly polymerized polyimide precursor solution can be obtained. If the polyesterimide precursor is excessively polymerized and the polymerization solution cannot be agitated easily, it may be diluted with the same solvent as deemed appropriate.

If the polyesterimide precursor proposed by the present invention is to be imidized and used as polyesterimide film, the polyesterimide precursor is desirably as highly polymerized as possible from the viewpoint of toughness. When polymerization occurs in the above monomer concentration range, the polymer is polymerized to a sufficiently high degree and sufficient monomer/polymer solubility can be ensured, as well. If polymerization occurs at concentrations below the above range, the polyesterimide precursor may not be polymerized to a high enough degree. If polymerization occurs at concentrations beyond the above range, on the other hand, solubility of monomers and the produced polymer may not be sufficient.

Also when the present invention is to be used as polyesterimide film, the intrinsic viscosity of the polyester imide precursor is preferably in a range of 0.1 to 20.0 dL/g, or more preferably in a range of 0.5 to 10.0 dL/g, from the viewpoint of toughness and handling of varnish.

When the polyesterimide precursor proposed by the present invention is manufactured, the diamine used, or specifically the diamine having the skeleton denoted by X representing a divalent aromatic group and/or aliphatic group in General Formula (2), is preferably an aromatic diamine and/or aliphatic diamine.

Aromatic diamines that can be used in the polymerization of polyesterimide precursor are not specifically limited as long as the required characteristics of polyester imide film can be met and the polymerization reactivity of polyesterimide precursor is not lost, where examples include such as p-phenylenediamine, m-phenylenediamine, 2,4-diaminotoluene, 2,5-diaminotoluene, 2,4-diaminoxylene, 2,4-diaminodulene, 4,4'-diaminodiphenylmethane, 4,4'-methylenebis (2-methylaniline), 4,4'-methylenbis (2-ethylaniline), 4,4'-methylenebis (2,6-dimethylaniline), 4,4'-methylenebis (2,6-diethylaniline), 4,4'-oxydianiline, 3,4'-oxydianiline, 3,3'-oxydianiline, 2,4'-oxydianiline, 4,4'-diaminodiphenylsulfone, 3,3'-diaminodiphenylsulfone, 4,4'-diaminobenzophenone, 3,3'-diaminobenzophenone, 4,4'-diaminobenzanilide, 4-aminophenyl-4'-aminobenzoate, benzidine, 3,3'-dihydroxybenzidine, 3,3'-dimethoxybenzidine, o-tolidine, m-tolidine, 2,2'-bis(trifluoromethyl)benzidine, 1,4-bis(4-aminophenoxy)benzene, 1,3-bis(4-aminophenoxy)benzene, 1,3-bis (3-aminophenoxy)benzene, 4,4'-bis(4-aminophenoxy) biphenyl, bis(4-(3-aminophenoxy)phenyl)sulfone, bis(4-(4-aminophenoxy)phenyl) sulfone, 2,2-bis(4-(4-aminophenoxy)phenyl)propane, 2,2-bis (4-(4-aminophenoxy)phenyl) hexafluoropropane, 2,2-bis(4-aminophenyl)hexafluoropropane, and p-terphenylenediamine. Two or more of the foregoing may be combined.

Just like the aromatic diamine, the aliphatic diamine is not specifically limited, where examples include 4,4'-methylenebis (cyclohexylamine), isophorone diamine, trans-1,4-diaminocyclohexane, cis-1,4-diaminocyclohexane, 1,4-cyclohexanebis (methylamine), 2,5-bis(aminomethyl)bicyclo [2.2.1]heptane, 2,6-bis(aminomethyl)bicyclo[2.2.1]heptane, 3,8-bis(aminomethyl)tricyclo[5.2.1.0]decane, 1,3-diaminoadamantane, 2,2-bis(4-aminocyclohexyl)propane, 2,2-bis (4-aminocyclohexyl)hexafluoropropane, 1,3-propoanediamine, 1,4-tetramethylenediamine, 1,5-pentamethylenediamine, 1,6-hexamethylenediamine, 1,7-heptamethylenediamine, 1,8-octamethylenediamine, 1,9-nonamethylenediamine, and the like. Two or more of the foregoing may be combined.

In the aforementioned aromatic diamine and/or aliphatic diamine, an aromatic diamine, or specifically a diamine whose X is an aromatic group, is preferred from the viewpoint of flame resistance. Also, it is more preferable that each aromatic group has no aliphatic group as a substituent, or the number of substituents is 1 or 2, where the substituent(s) is/are preferably alkyl group(s) such as a methyl group or the like. From the viewpoint of expression of low heat expansion characteristics in polyesterimide film, it is preferable to use a diamine having a rigid, linear structure such as p-phenylenediamine, 2,5-diaminotoluene, 3,4'-oxydianiline, 4,4'-diaminobenzanilide, 4-aminophenyl-4'-aminobenzoate, benzidine, 3,3'-dihydroxybenzidine, 3,3'-dimethoxybenzidine, o-tolidine, m-tolidine, 2,2'-bis trifluoromethyl)benzidine, p-terphenylenediamine or trans-1,4-diaminocyclohexane. At this time, the content of any such rigid diamine is 10 to 100 percent by mol, or preferably 50 to 90 percent by mol, relative to the total amount of diamine used.

For the polyesterimide precursor pertaining to the present invention, any aromatic tetracarboxylic acid dianhydride and/or aliphatic tetracarboxylic acid dianhydride may be combined as a co-polymerization component, other than the ester group-containing tetracarboxylic acid dianhydride proposed by the present invention and expressed by General Formula (1) as an acid dianhydride, to the extent that the polymerization reactivity or any of the required characteristics of polyesterimide is not significantly lost. Aromatic tetracarboxylic acid dianhydrides that can be used for this purpose are not specifically limited, where examples include such as pyromellitic dianhydride, 3,3',4,4'-biphenyltetracarboxylic acid dianhydride, hydroquinone-bis (trimellitateanhydride), methylhydroquinone-bis(trimellitateanhydride), 3,3',4,4'-benzophenonetetracarboxylic acid dianhydride, 3,3',4,4'-biphenylether tetracarboxylic acid dianhydride, 3,3',4,4'-biphenylsulfonetetracarboxylic acid dianhydride, 2,2'-bis(3,4-dicarboxyphenyl) hexafluoropropanoic acid dianhydride, 2,2'-bis(3,4-dicarboxyphenyl) propanoic acid dianhydride, 1,4,5,8-naphthalenetetracarboxylic acid dianhydride, 2,3,6,7-naphthalenetetracarboxylic acid dianhydride, 4,4'-bis(1,3-dioxo-1,3-dihydroisobenezofuran-5-ylcarbonyl oxy)biphenyl, 4,4'-bis(1,3-dioxo-1,3-dihydroisobenzofuran-5-ylcarbonyloxy)-3,3'-dimethylbiphenyl, 4,4''-bis(1,3-dioxo-1,3-dihydroisobenzofuran-5-ylcarbonyloxy)-3-methyl-p-terphenyl and 4,4''-bis(1,3-dioxo-1,3-dihydroisobenzofuran-5-ylcarbonyloxy)-3,3'''-dimethyl-p-quarterphenyl. Two or more of the foregoing may be used.

Also, aliphatic tetracarboxylic acid dianhydrides that can be used are not specifically limited, where examples include bicyclo[2.2.2]octo-7-en-2,3,5,6-tetracarboxylic acid dianhydride, 5-(dioxotetrahydrofuryl-3-methyl-3-cyclohexene-1,2-dicarboxylic acid anhydride, 4-(2,5-dioxotetrahydrofuran-3-yl)-tetralin-1,2-dicarboxylic acid anhydride, tetrahydrofuran-2,3,4,5-tetracarboxylic acid dianhydride, bicyclo-3,3',4,4'-tetracarboxylic acid dianhydride, 1,2,4,5-cyclohexanetetracarboxylic acid dianhydride, 1,2,3,4-cyclobutanetetracarboxylic acid dianhydride, 1,2,3,4-cyclopentanetetracarboxylic acid dianhydride, and the like. Two or more of the foregoing may be combined.

If any of the above aromatic tetracarboxylic acid dianhydrides and/or aliphatic tetracarboxylic acid dianhydrides is used as a co-polymerization component, other than the ester group-containing tetracarboxylic acid dianhydride proposed by the present invention, its or their content is 0 to 50 percent by mol, or preferably 0 to 30 percent by mol, of the total amount of tetracarboxylic acid dianhydride used.

The solvent used in the polymerization reaction is preferably an aprotic solvent such as N,N-dimethylformamide, N,N-dimethylacetamide, N-methyl-2-pyrrolidone, dimethyl sulfoxide or the like, but it is not specifically limited and any solvent can be used as long as the material monomers and the produced polyimide precursor can be dissolved. Solvents that can be used include, among others: amide solvents such as N,N-dimethylformamide, N,N-dimethylacetamide, N-methyl-2-pyrrolidone, 1,3-dimethyl-2-imidazolidinone or the like; cyclic ester solvents such as γ-butyrolactone, γ-valerolactone, δ-valerolactone, γ-caprolactone, ∈-caprolactone, α-methyl-γ-butyrolactone or the like; carbonate solvents such as ethylene carbonate, propylene carbonate or the like; ether solvents such as diglyme, triglyme or the like; phenol solvents such as m-cresol, p-cresol, 3-chlorophenol, 4-chlorophenol or the like; and sulfone solvents such as sulfolane, dimethylsulfoxide or the like.

A polymerization solution of the polyesterimide precursor proposed by the present invention may be dripped into a large amount of water, poor solvent such as methanol or the like and then filtered and dried to be isolated as powder.

Next, the polyesterimide proposed by the present invention and expressed by General Formula (3) above can be manufactured by putting the polyesterimide precursor under the present invention, as obtained by the aforementioned method, through dehydrative ring-closure reaction (imidization reaction). This imidization reaction can be implemented using any known method, but in the case of the present invention, it is preferable to imidize the polyesterimide precursor proposed by the present invention by means of heating or using a cyclodehydration reagent.

First, the method to manufacture polyesterimide film is explained. Specifically, a polymerization solution (varnish) of the polyesterimide precursor is poured and spread over a substrate of glass, copper, aluminum, stainless, silicon, etc., and then dried in an oven at 40 to 180° C., or preferably at 50 to 150° C. The obtained polyesterimide precursor film is then heated on the substrate in vacuum, in inert gas such as nitrogen, or in air, at 200 to 450° C., or preferably at 250 to 430° C., to manufacture the polyesterimide film conforming to the present invention. The heating temperature is preferably 200° C. or above to ensure that sufficient ring-closing reaction is caused to achieve imidization, or 450° C. or below to ensure thermal stability of the produced polyesterimide film. Also, imidization is desirably performed in vacuum or inert gas to suppress breakdown by thermal oxidization, but it can also be performed in air so long as the imidization temperature is not too high.

Imidization reaction can also be implemented, in place of using heat treatment such as the above, by soaking the polyesterimide precursor film in a solution containing a cyclodehydration reagent such as acetic anhydride or the like in the presence of a tertiary amine such as pyridine, triethylamine or the like. Such cyclodehydration reagent can also be introduced to the varnish of polyesterimide precursor and agitated beforehand at room temperature, after which the mixture can be poured and spread over the aforementioned substrate and dried, to create partially imidized polyesterimide precursor film. When this film is heat-treated as explained above, polyesterimide film is obtained.

If the polyimide dissolves in its own solvent when varnish of a polymerization solution of polyesterimide precursor is heated directly to 150 to 230° C., or when the solution is diluted with the same solvent to an appropriate degree and then its varnish is heated to 150 to 230° C., then varnish of the polyesterimide proposed by the present invention can be manufactured with ease. If the polyimide does not dissolve in the solvent, powder of the polyesterimide can be precipitated. In this case, toluene, xylene, etc., may be added to remove by-products of imidization such as water and the like through azeotropy and distillation. A base such as γ-picoline or the like may also be added as a catalyst. It is also possible to drip varnish of polyesterimide into a large amount of water, poor solvent such as methanol or the like to cause the polyesterimide to precipitate, and then filter out the precipitates to isolate the polyesterimide as powder. If the polyesterimide powder is soluble in the aforementioned polymerization solvent, it can be dissolved again in the solvent to produce polyesterimide varnish.

The polyesterimide proposed by the present invention can also be manufactured in a single step by causing the ester group-containing tetracarboxylic acid dianhydride and diamine to react in solvent at high temperature (one-pot polymerization), without isolation of the polyesterimide precursor. In this case, it is better that the reaction temperature is kept in a range of 130 to 250° C., or preferably in a range of 150 to 230° C., to promote the reaction. If the polyesterimide is insoluble in the solvent used, it can be obtained as precipitate. If the polyesterimide is soluble in the solvent, it can be obtained as polyesterimide varnish. Solvents that can be used in one-pot polymerization are not specifically limited, and examples of solvents include aprotic solvents such as N,N-dimethylformamide, N,N-dimethylacetamide, N-methyl-2-pyrrolidone, dimethylsulfoxide and the like. In addition to the above, phenolic solvents such as m-cresol and the like can also be used. Toluene, xylene, etc., may be added to these solvents to remove water, which is a by-product due to imidization, through azeotropy and distillation. A base such as γ-picoline or the like may also be added as an imidization catalyst. It is also possible to drip the obtained varnish into a large amount of water, poor solvent such as methanol or the like and filter out the precipitates to isolate the polyesterimide as powder. If the polyesterimide is soluble in the aforementioned solvent, its powder can be dissolved again in the solvent to produce polyesterimide varnish.

Polyesterimide film can also be formed by applying varnish of the polyesterimide obtained above onto a substrate and then drying the substrate at 40 to 400° C. or preferably at 100 to 350° C.

Additionally, a polyesterimide molding can be produced by heating and compressing powder of the polyesterimide obtained above at 200 to 450° C. or preferably at 250 to 430° C.

Another way to form polyesterimide is to add a dehydration reagent such as N,N-dicyclohexyl carbodiimide, trifluoroacetic acid anhydride or the like into a polyesterimide precursor solution and agitate the solution to cause reaction at 0 to 100° C. or preferably at 20 to 60° C., to form polyester isoimide which is an isomer of polyesterimide. Isoimidization reaction can also be achieved by soaking film of the polyesterimide precursor in a solution containing the above dehydration reagent. After varnish of the polyesterisoimide is made into film according to a procedure similar to the one explained above, the film can be heat-treated at 250 to 450° C.

or preferably at 270 to 400° C. to cause isomerization reaction, thereby converting polyesterisoimide to polyesterimide with ease.

To apply the polyesterimide proposed by the present invention as an insulation substrate material for FPC, TAB or COF, the polyesterimide film conforming to the present invention, in terms of the material performance, has a coefficient of linear thermal expansion of preferably 30 ppm/K or less, or more preferably 20 ppm/K or less. Also, the coefficient of water absorption is preferably 1.0% or less, or more preferably 0.5% or less. The coefficient of hygroscopic expansion is preferably 10 ppm/RH % or less, or more preferably 5 ppm/RH % or less. The glass transition temperature is preferably 300° C. or above from the viewpoint of solder heat resistance, or more preferably 350° C. or above. As for the 5% weight reduction temperature in air which is an indicator of thermal oxidization stability, basically the higher this temperature, the better. However, no material problems occur as long as the temperature is 450° C. or above. Flame resistance preferably meets the V-0 level according to the UL-94 standard. In TAB and COF applications, the elastic modulus of polyesterimide film is not specifically limited. In FPC application, however, the lower the elastic modulus, the better from the viewpoint of low repulsion, where a preferred level is 4 GPa or less. As an indicator of film flexibility, once the breaking resistance is confirmed to be available in the 180° bending test, applicability in the above industrial fields is ensured. As for breaking elongation measured by the tensile test, the greater the elongation, the better because the scope of application will expand. Particularly in FPC applications where the polyesterimide film must be bent for mounting, a breaking elongation of 10% or more ensures applicability of the film. However, a breaking elongation of 20% or more is preferred and that of 50% or more is more preferred.

When producing a CCL by forming a polyesterimide layer per the present invention directly on the copper foil, the peel strength of the CCL, which is an indicator of adhesive strength, is preferably 0.8 kgf/cm or more, or more preferably 1.0 kgf/cm or more.

As necessary, an additive such as an oxidization stabilizer, filler, adhesion promoter, silane coupling agent, photosensitizer, photo-polymerization initiator, sensitizer, terminal sealant, cross-linking agent or the like may be added to the polyesterimide and its precursor under the present invention.

EXAMPLES

The present invention is specifically explained below using examples, but it should be noted that the present invention is not at all limited to those examples. Physical properties in the examples below were measured by the methods specified below.

<Infrared Absorption Spectrum>

A Fourier transform infrared spectrophotometer (FT-IR5300 or FT-IR350 manufactured by JASCO) was used to measure the infrared absorption spectrum of ester group-containing tetracarboxylic acid dianhydride based on the KBr method. Additionally, measurement of infrared absorption spectrum was also performed on the polyesterimide precursor and thin polyesterimide film (about 5 μm thick) based on the transmission method.

<$^1$H-NMR Spectrum>

An NMR spectrophotometer manufactured by JEOL (ECP400) was used to measure the $^1$H-NMR spectrum of ester group-containing tetracarboxylic acid dianhydride in deuterated-dimethyl sulfoxide (DMSO-$d_6$).

<Element Analysis>

An organic element analyzer manufactured by Yanaco Technical Science (CHN CORDER MT-6) was used to perform element analysis on the ester group-containing tetracarboxylic acid dianhydride proposed by the present invention, to obtain the contents of carbon, hydrogen and nitrogen (percent by weight), respectively.

<Differential Scanning calorimetry>

A differential scanning calorimetric (DSC) analyzer manufactured by Bruker AXS (DSC3100) was used to measure the melting point and melting curve of ester group-containing tetracarboxylic acid dianhydride in nitrogen atmosphere by raising the temperature at a rate of 5° C./min. The higher the melting point and sharper the melting peak, the higher the purity is.

<Intrinsic Viscosity>

An Ostwald viscometer was used to measure a 0.5% solution (percent by weight) of polyesterimide precursor at 30° C. The obtained reduced viscosity was taken as the intrinsic viscosity.

<Glass Transition Temperature: Tg>

A thermo-mechanical analyzer manufactured by Bruker AXS (TMA4000) was used to perform dynamic viscoelasticity measurement, obtaining the glass transition temperature of polyesterimide film (20 μm thick) from the peak of the loss energy curve drawn at a frequency of 0.1 Hz and temperature rise rate of 5° C./min. Alternately, a static load of 0.5 g per 1 μm of film thickness was applied to a test piece and temperature was raised at a rate of 5° C./min to create a TMA curve showing the relationship of test piece elongation and the temperature, after which two tangential lines were drawn near the temperature where the test piece began elongating rapidly and their point of intersection was identified to obtain the glass transition temperature.

<Coefficient of Linear Thermal Expansion: CTE>

A thermo-mechanical analyzer manufactured by Bruker AXS (TMA4000) was used to perform thermo-mechanical analysis, obtaining the coefficient of linear thermal expansion of polyesterimide film (20 μm thick), as an average value over a temperature range of 100 to 200° C., from the elongation of the test piece when a load of 0.5 g per 1 μm of film thickness was applied and the temperature was raised at a rate of 5° C./min.

<5% Weight Reduction Temperature: Td5)

A thermogravimetric analyzer manufactured by Bruker AXS (TG-DTA2000) was used to measure the temperature at which the initial weight of polyesterimide film (20 μm thick) dropped by 5%, both in nitrogen and air, at a temperature rise rate of 10° C./min. The higher this temperature, the greater the thermal stability was.

<Dielectric Constant: ∈cal>

An Abbe refractometer manufactured by Atago (Abbe 4T) was used to measure the index of refraction of polyesterimide film (20 μm thick) in the direction parallel to the film (nin) and direction vertical to the film (nout) (using a sodium lamp at a wavelength of 589 nm), after which the dielectric constant (∈cal) of polyesterimide film was calculated at 1 MHz according to the empirical formula: $\epsilon_{cal} = 1.1 \times n_{av}^2$, based on the average index of refraction of polyesterimide film [$n_{av} = (2n_{in} + n_{out})/3$].

<Coefficient of Water Absorption>

Polyesterimide film (20 to 30 μm thick) that had been vacuum-dried for 24 hours at 50° C. was soaked in 24° C. water for 24 hours, after which the excess moisture was wiped off and the coefficient of water absorption (%) was obtained from the weight increase. In most applications, the smaller this value, the better.

<Coefficient of Hygroscopic Expansion: CHE>

A test piece of polyesterimide film (5 mm×20 mm×20 μm thick) that had been vacuum-dried for several hours at 100° C. was promptly set on a thermo-mechanical analyzer (TMA4000) manufactured by Bruker AXS (at a distance of 15 mm between chucks), and then a static load of 0.5 g per 1 μm of film thickness was applied to the test piece and dry nitrogen was introduced at room temperature for 1 hour, after which a precision moisture feeder manufactured by Shinyei (SRG-1R-1) was used to introduce wet gas of 80% relative humidity (RH) into the TMA4000 system, obtaining the coefficient of hygroscopic expansion of polyesterimide film from the elongation of the test piece at room temperature; the smaller this value, the higher the hygroscopic dimensional stability.

<Elastic Modulus, Breaking Elongation, Breaking Strength>

A tensile tester manufactured by Toyo Baldwin (Tensilon UTM-2) was used to conduct the tensile test (at an elongation speed of 8 mm/min) on a test piece of polyesterimide (3 mm×30 mm×20 μm thick), obtaining the elastic modulus from the initial slope of the stress vs. strain curve, and the breaking elongation (%) from the rate of elongation at which the film broke. The greater the breaking elongation, the higher the toughness of film.

<Flame Resistance Evaluation>

Flame resistance was evaluated on a test piece of polyesterimide (125 mm×13 mm×20 μm thick) according to the UL-94V standard.

<Peel Test: Peel Strength>

A CCL was created as follows. Specifically, an NMP solution of the polyesterimide precursor proposed by the present invention was applied onto a matte surface of electrolytic copper foil (F3-WS manufactured by Furukawa Electric; 18 μm thick), after which the copper foil was dried in air at 80° C. for 3 hours and then thermally imidized for 1 hour in vacuum at the specified temperature to obtain a test piece. The 180° peel test was conducted on test pieces, each produced as above, under the same conditions as those used in the aforementioned tensile test to measure the peel strength.

Example 1

<Synthesis of Ester Group-Containing Tetracarboxylic Acid Dianhydride (TAOPP-BP)>
Formula (6):

[Chemical 6]

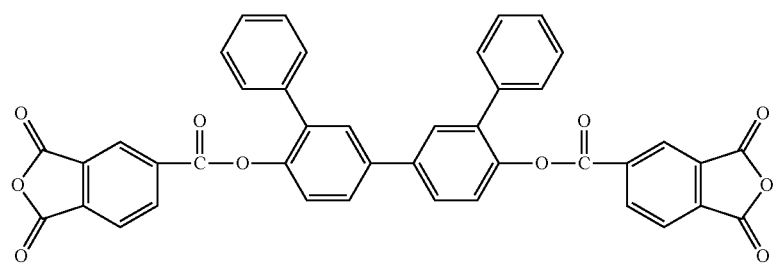

(6)

Ester group-containing tetracarboxylic acid dianhydride expressed by this formula (hereinafter referred to as "TAOPP-BP") was synthesized as follows. First, 10.11 g (48 mmol) of trimellitic anhydride chloride was dissolved in 45.5 mL of dewatered tetrahydrofuran (THF) in an egg-plant flask, and then the flask was sealed with a septum cap to prepare solution A. In a different flask, 6.77 g (20 mmol) of diol expressed by Formula (10) (hereinafter referred to as "OPP-BP") was dissolved in 68.5 mL of THF, to which 9.7 mL (120 mmol) of pyridine was added and the flask was sealed with a septum cap to prepare solution B.

Solution B was slowly dripped into solution A in a syringe under cooling in an ice bath and also under agitation, after which the mixture was agitated for 12 hours at room temperature. After the reaction, white precipitates (pyridine hydrochloride) were filtered out and the filtrate was condensed with an evaporator, after which the condensed filtrate was dripped into water and the precipitates were washed with water repeatedly and then vacuum-dried for 12 hours at 160° C. to obtain a crude product in the form of a yellow powder (yield: 99%). This powder was then recrystallized from acetic anhydride and the obtained crystals were washed with acetic anhydride and toluene, and finally vacuum-dried for 12 hours at 160° C. to obtain yellow crystal. Based on the FT-IR spectrum and $^1$H-NMR spectrum, the obtained product was confirmed to be the target ester group-containing tetracarboxylic acid dianhydride (TAOPP-BP) expressed by Formula (6) above. The sharp melting peak identified by the DSC measurement indicates high purity of the product. The $^1$H-NMR spectrum of this ester group-containing tetracarboxylic acid dianhydride is shown in FIG. 11.

FT-IR (KBr): 1858 cm$^{-1}$ and 1784 cm$^{-1}$ (acid anhydride group C=O stretching vibration absorption band), 1744 cm$^{-1}$ (ester group C=O stretching vibration absorption band), 1476 cm$^{-1}$ (phenyl group and phenylene group skeletal vibration absorption band), 1223 cm$^{-1}$ (C—O-Ph stretching vibration absorption band)

[Chemical 6-1]

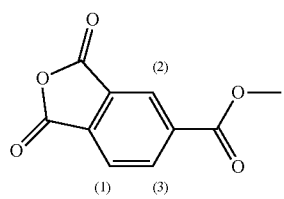

(6-1)

$^1$H-NMR (DMSO-d6): δ8.53 to 8.55 ppm [aromatic protons in Formula (6-1) (1), d, 2H], δ8.49 ppm [aromatic protons in Formula (6-1) (2), s, 2H, total 4H of protons in Formula (6-1) (1)+(2) above: relative integral intensity 4.16, δ8.23 to 8.25 ppm [aromatic protons in Formula (6-1) (3), d, 2H, relative integral intensity 2.00], δ7.93 to 7.97 ppm (aromatic protons at 2,2'6,6' positions of 4,4'-biphenylene group at center, 4H, relative integral intensity 4.16), δ7.62 to 7.65 ppm (aromatic protons at 2,4,6 position of phenyl substitution group, m, 6H, relative integral intensity 6.22), δ7.30 to 7.40 ppm (aromatic protons at 3,3' positions of 4,4'-biphenylene group at center 2H+aromatic protons at 3,5 positions of phenyl substitution group 4H, m, total 6H, relative integral intensity 6.08)

DSC: Melting point 236.9° C.

Example 2

<Synthesis of Ester Group-Containing Tetracarboxylic Acid Dianhydride (TADHTP-Ph)>
Formula (7):

[Chemical 7]

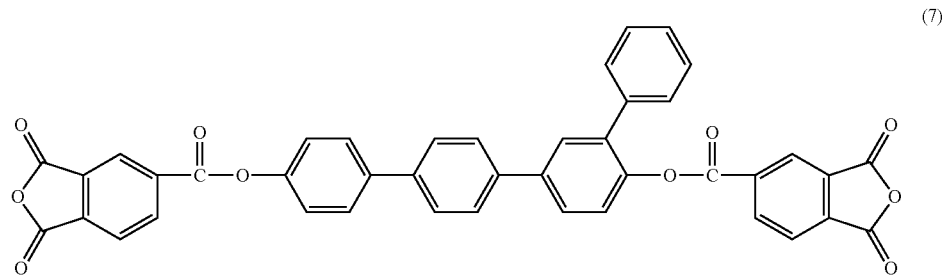

(7)

Ester group-containing tetracarboxylic acid dianhydride expressed by this formula (hereinafter referred to as "TADHTP-Ph") was synthesized as follows. First, 10.10 g (48 mmol) of trimellitic anhydride chloride was dissolved in 45.5 mL of dewatered THF in an egg-plant flask, and then the flask was sealed with a septum cap to prepare solution A. In a different flask, 6.77 g (20 mmol) of diol expressed by Formula (11) (hereinafter referred to as "DHTP-Ph") was dissolved in 68.5 mL of THF, to which 9.7 mL (120 mmol) of pyridine was added and the flask was sealed with a septum cap to prepare solution B.

Solution B was slowly dripped into solution A in a syringe under cooling in an ice bath and also under agitation, after which the mixture was agitated for 12 hours at room temperature. After the reaction, white precipitates (pyridine hydrochloride) were filtered out and the filtrate was condensed with an evaporator, after which the condensed filtrate was dripped into water and the precipitates were washed with water repeatedly and then vacuum-dried for 12 hours at 160° C. to obtain a crude product in the form of a white powder (yield: 71%). This powder was then recrystallized twice from γ-butyrolactone/toluene mixture solvent (volume ratio: 1/6) and the obtained crystals were washed with the same solvent, and finally vacuum-dried for 12 hours at 160° C. to obtain white crystals. Based on the FT-IR spectrum and $^1$H-NMR spectrum, the obtained product was confirmed to be the target ester group-containing tetracarboxylic acid dianhydride (TADHTP-Ph) expressed by Formula (7) above. The sharp melting peak identified by the DSC measurement indicates high purity of the product. The $^1$H-NMR spectrum of this ester group-containing tetracarboxylic acid dianhydride is shown in FIG. 12.

FT-IR (KBr): 1865 cm$^{-1}$ and 1782 cm$^{-1}$ (acid anhydride group C=O stretching vibration absorption band), 1736 cm$^{-1}$ (ester group C=O stretching vibration absorption band), 1480 cm$^{-1}$ (phenyl group and phenylene group skeletal vibration absorption band), 1227 cm$^{-1}$ (C—O-Ph stretching vibration absorption band)

DSC: Melting point 250.0° C.

| Element analysis results | Theoretical values | C: 77.47%, H: 3.23% |
|---|---|---|
| | Analysis values | C: 77.49%, H: 3.38% |

Example 3

<Synthesis of Ester Group-Containing Tetracarboxylic Acid Dianhydride (TADHQP-DP)>
Formula (8):

[Chemical 8]

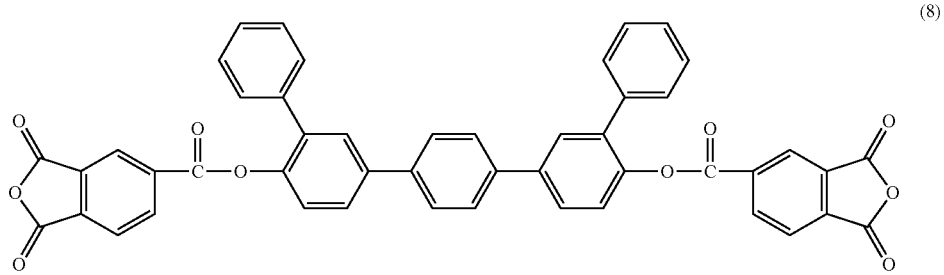

(8)

Ester group-containing tetracarboxylic acid dianhydride expressed by this formula (hereinafter referred to as "TADHQP-DP") was synthesized as follows. First, 5.05 g (24 mmol) of trimellitic anhydride chloride was dissolved in 3.28 mL of dewatered N,N-dimethylacetamide (DMAc) in an eggplant flask, and then the flask was sealed with a septum cap to prepare solution A. In a different flask, 5.24 mL of DMAc and 3.24 mL (40 mmol) of pyridine were added to 4.91 g (10 mmol) of diol expressed by Formula (12) (hereinafter referred to as "DHQP-DP"), which was then dissolved by heating to 110° C., and then the flask was sealed with a septum cap to prepare solution B.

Before precipitates generated, solution B was added to solution A and then 2 mL of DMAc was added and the mixture was agitated for 12 hours at room temperature. After the reaction, the mixture was dripped into water and the precipitates were washed repeatedly with water and then vacuum-dried for 12 hours at 160° C. to obtain a crude product in the form of a light-yellow powder (yield: 97%). This powder was then recrystallized twice from 1,4-dioxane/toluene mixture solvent (volume ratio: 2/3) and the obtained crystals were washed with the same solvent, and finally vacuum-dried for 12 hours at 160° C. to obtain yellow, needle-like crystals. Based on the FT-IR spectrum and $^1$H-NMR spectrum, the obtained product was confirmed to be the target ester group-containing tetracarboxylic acid dianhydride (TADHQP-DP) expressed by Formula (8) above. The sharp melting peak identified by the DSC measurement indicates high purity of the product. The $^1$H-NMR spectrum of this ester group-containing tetracarboxylic acid dianhydride is shown in FIG. 13.

FT-IR (KBr): 1861 cm$^{-1}$ and 1784 cm$^{-1}$ (acid anhydride group C=O stretching vibration absorption band), 1746 cm$^{-1}$ (ester group C=O stretching vibration absorption band), 1478 cm$^{-1}$ (phenyl group and phenylene group skeletal vibration absorption band), 1223 cm$^{-1}$ (C—O-Ph stretching vibration absorption band)

DSC: Melting point 278.3° C.

| Element analysis results | Theoretical values | C: 77.32%, H: 3.60% |
|---|---|---|
| | Analysis values | C: 77.26%, H: 3.66% |

Example 4

<Polymerization and Imidization of Polyesterimide Precursor and Characteristics Evaluation of Polyesterimide Film>

Into a well-dried sealed reaction container with agitator, 5 mmol of p-phenylenediamine as introduced and then dissolved in fully-dewatered N-methyl-2-pyrrolidone (NMP) using molecularsieve 4 A, after which 5 mmol of the ester group-containing tetracarboxylic acid dianhydride (TAOPP-BP) expressed by Formula (6) in powder form, as described in Example 1, was slowly added to this solution (total monomer concentration: 22.7 percent by weight). Since the reaction solution became increasingly viscous and difficult to agitate, the same solvent was added gradually to dilute the solution to a final total monomer concentration of 15.2 percent by weight. The solution was agitated for 72 hours to obtain a uniform, viscous polyesterimide precursor solution. When this polyesterimide precursor solution was let stand for one month at room temperature and −20° C., no precipitation or gelling occurred, indicating high storage stability of the solution. When measured in NMP with an Ostwald viscometer at 30° C. and concentration of 0.5 percent by weight, the polyesterimide precursor had a intrinsic viscosity of 1.84 dL/g, suggesting a high-polymer. This polyesterimide precursor solution was applied on a glass substrate and dried at 80° C. for 2 hours to obtain polyesterimide precursor film, which was then thermally imidized on the substrate under reduced pressure for 1 hour at 250° C., and another 1 hour at 300° C., after which the film was separated from the substrate to remove any residual stress and then heat-treated for 1 hour at 340° C. to obtain a light-yellow, transparent polyesterimide film of 19 μm in film thickness. This polyesterimide film did not break in the 180° bending test, exhibiting flexibility. Also, it did not dissolve at all in any organic solvent. When the dynamic viscoelasticity was measured on this polyesterimide film, a glass transition point (determined from the loss peak on the dynamic viscoelasticity curve) was observed at 389° C.

Also, the coefficient of linear thermal expansion was low at 18.8 ppm/K. The dielectric constant estimated from the average index of refraction was 2.81, which is lower than the dielectric constant (3.3) of the most generally used conventional polyimide film (KAPTON-V manufactured by Toray/DuPont). The 5% weight reduction temperature was also high, at 474° C. in nitrogen and 468° C. in air, indicating sufficiently high heat resistance. In addition, the polyesterimide film proposed by the present invention had a very low coefficient of water absorption of 0.26%, and the coefficient of hygroscopic expansion of 3.9 ppm/RH % was also much lower than that of KAPTON-V film (coefficient of water absorption 2.9%, coefficient of hygroscopic expansion 24 ppm/RH %). As for mechanical characteristics, the tensile elastic modulus (Young's modulus) was 4.32 GPa, which indicates a relatively low value; while the breaking strength was 0.194 GPa, and the breaking elongation also was 12.1%. Furthermore, the peel strength measured on a CCL created via thermal imidization in vacuum for 1 hour at 400° C. was 0.93 kgf/cm, demonstrating very high adhesion strength for a polyimide having a rigid skeleton.

As shown above, this polyesterimide had an extremely low coefficient of linear thermal expansion, very low coefficient of water absorption, very low coefficient of hygroscopic expansion, high thermal stability, relatively low elastic modulus and relatively low dielectric coefficient. Also, its flame resistance conformed to the V-0 level per UL-94. The physical properties are summarized in Table 1. The infrared absorption spectrum of thin film of this polyesterimide is shown in FIG. 1.

Example 5

A polyesterimide precursor was polymerized, made into film, and imidized, to create polyesterimide film according to the method described in Example 4 by using 4-aminophenyl-4'-aminobenzoate (hereinafter referred to as "APAB") instead of p-phenylenediamine as the diamine component, and then the physical properties of the film were evaluated in the same manner. The physical properties are shown in Table 1. The infrared absorption spectrum of thin film of this polyesterimide is shown in FIG. 2.

Example 6

A polyesterimide precursor was polymerized, made into film, and imidized, to create polyesterimide film according to the method described in Example 4 by using m-tolidine instead of p-phenylenediamine as the diamine component, and then the physical properties of the film were evaluated in the same manner. The physical properties are shown in Table 1. The infrared absorption spectrum of thin film of this polyesterimide is shown in FIG. 3.

Example 7

A polyesterimide precursor was polymerized, made into film, and imidized, to create polyesterimide film according to the method described in Example 4 by using o-tolidine instead of p-phenylenediamine as the diamine component, and then the physical properties of the film were evaluated in the same manner. The physical properties are shown in Table 1. The infrared absorption spectrum of thin film of this polyesterimide is shown in FIG. 4.

Example 8

A polyesterimide precursor was polymerized, made into film, and imidized, to create polyesterimide film according to the method described in Example 4 by using TADHTP-Ph instead of TAOPP-BP as the ester group-containing tetracarboxylic acid dianhydride, and by using p-phenylenediamine as the diamine component, and then the physical properties of the film were evaluated in the same manner. The physical properties are shown in Table 1. The infrared absorption spectrum of thin film of this polyesterimide is shown in FIG. 5.

Example 9

A polyesterimide precursor was polymerized, made into film, and imidized, to create polyesterimide film according to the method described in Example 4 by using TADHTP-Ph as the ester group-containing tetracarboxylic acid dianhydride and o-tolidine as the diamine component, and then the physical properties of the film were evaluated in the same manner. The physical properties are shown in Table 1. The infrared absorption spectrum of thin film of this polyesterimide is shown in FIG. 6.

Example 10

A polyesterimide precursor was polymerized, made into film, and imidized, to create polyesterimide film according to the method described in Example 4 by using TADHQP-DP as the ester group-containing tetracarboxylic acid dianhydride and p-phenylenediamine as the diamine component, and then the physical properties of the film were evaluated in the same manner. The physical properties are shown in Table 1. The infrared absorption spectrum of thin film of this polyesterimide is shown in FIG. 7.

Example 11

A polyesterimide precursor was polymerized, made into film, and imidized, to create polyesterimide film according to the method described in Example 4 by using TADHQP-DP as the ester group-containing tetracarboxylic acid dianhydride and APAB as the diamine component, and then the physical properties of the film were evaluated in the same manner. The physical properties are shown in Table 1. The infrared absorption spectrum of thin film of this polyesterimide is shown in FIG. 8.

Example 12

A polyesterimide precursor was polymerized, made into film, and imidized, to create polyesterimide film according to the method described in Example 4 by using TADHQP-DP as the ester group-containing tetracarboxylic acid dianhydride and m-tolidine as the diamine component, and then the physical properties of the film were evaluated in the same manner. The physical properties are shown in Table 1. The infrared absorption spectrum of thin film of this polyesterimide is shown in FIG. 9.

Example 13

A polyesterimide precursor was polymerized, made into film, and imidized, to create polyesterimide film according to the method described in Example 4 by using TADHQP-DP as the ester group-containing tetracarboxylic acid dianhydride and o-tolidine as the diamine component, and then the physical properties of the film were evaluated in the same manner. The physical properties are shown in Table 1. The infrared absorption spectrum of thin film of this polyesterimide is shown in FIG. 10.

Example 14

A polyesterimide precursor was randomly co-polymerized by simultaneously adding TADHQP-DP (2.5 mmol) and TA44BP (2.5 mmol) expressed by Formula (13) shown later, both in powder form, to an NMP solution of p-phenylenediamine (5 mmol), and then made into film, and imidized, to create polyesterimide film according to the method described in Example 4, and then the physical properties of the film were evaluated in the same manner. The physical properties are shown in Table 1.

Example 15

A polyesterimide precursor was randomly co-polymerized by simultaneously adding TADHQP-DP (3.5 mmol) and TA44BP (1.5 mmol), both in powder form, to an NMP solution of p-phenylenediamine (5 mmol), and then made into film, and imidized, to create polyesterimide film according to the method described in Example 4, and then the physical properties of the film were evaluated in the same manner. The physical properties are shown in Table 1.

Example 16

A chain-controlled polyesterimide precursor co-polymer having a different chain than that of a random co-polymer was polymerized by adding TA44BP (1.5 mmol) in powder form to an NMP solution of p-phenylenediamine (5 mmol) and causing it to react for 2 hours at room temperature and then adding TADHQP-DP (3.5 mmol) also in powder from, after which it was made into film, and imidized, to create polyesterimide film according to the method described in Example 4, and then the physical properties of the film were evaluated in the same manner. The physical properties are shown in Table 1.

Example 17

A polyesterimide precursor was randomly co-polymerized by simultaneously adding TADHQP-DP (2.5 mmol) and TA44BP (2.5 mmol), both in powder form, to an NMP solution containing p-phenylenediamine (2.5 mmol) and 4,4'-oxydianilin (2.5 mmol), and then made into film, and imidized, to create polyesterimide film according to the method described in Example 4, and then the physical properties of the film were evaluated in the same manner. The physical properties are shown in Table 1.

Comparative Example 1

A polyesterimide precursor was polymerized by using p-phenylenediamine as the diamine and also using, as the tetracarboxylic acid dianhydride, the ester group-containing tetracarboxylic acid dianhydride having no substituent as expressed by Formula (13) below, after which it was made into film and imidized to create polyesterimide film according to the method described in Example 4, and then the physical properties of the film were evaluated in the same manner:

[Chemical 13]

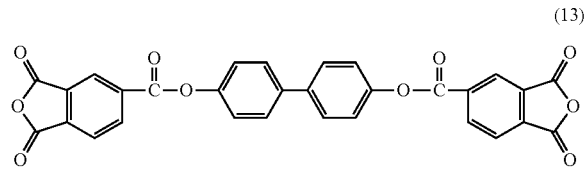

(13)

The physical properties are shown in Table 1. Although the CTE value is extremely low, because of this the elastic modulus is very high at 6.68 GPa. This is due to use of the ester group-containing tetracarboxylic acid dianhydride having no phenyl substituent. In addition, the breaking elongation is low at 3.5%, while the coefficient of water absorption is high at 0.78%, indicating that these physical properties are inferior to those of the polyesterimide film in Example 4 conforming to the present invention.

Comparative Example 2

A polyesterimide precursor was polymerized by using p-phenylenediamine as the diamine and also using, as the tetracarboxylic acid dianhydride, the ester group-containing tetracarboxylic acid dianhydride having methyl substitution groups as expressed by Formula (14) below, after which it was made into film and imidized to create polyesterimide film according to the method described in Example 4, and then the physical properties of the film were evaluated in the same manner:

[Chemical 14]

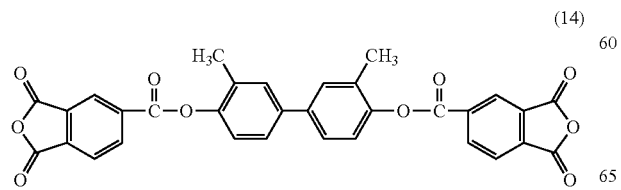

(14)

The physical properties are shown in Table 1. Although the CTE value is extremely low, because of this the elastic modulus is very high at 6.21 GPa. This is due to use of the ester group-containing tetracarboxylic acid dianhydride having no phenyl substitution group. In addition, the breaking elongation is low at 7.3%, while the coefficient of water absorption is high at 0.71%, indicating that these physical properties are inferior to those of the polyesterimide film in Example 4 conforming to the present invention.

TABLE 1

|  | [η] (dL/g) | CTE (ppm/K) | Tg (° C.) | Coefficient of water absorption (%) | CHE (ppm/ RH %) | $Td^5$ $N_2$ (° C.) | $Td^5$ air (° C.) | Elastic modulus (GPa) | Breaking elongation (%) | Flame resistance (V-0) | ε cal |
|---|---|---|---|---|---|---|---|---|---|---|---|
| Example 4 | 1.84 | 18.8 | 389 | 0.26 | 3.86 | 474 | 468 | 4.32 | 12.1 | ○ | 2.81 |
| Example 5 | 1.14 | 24.4 | 342 | 0.43 |  | 465 | 463 | 3.80 | 13.1 |  | 2.91 |
| Example 6 | 1.78 | 24.4 | 349 | 0.46 |  | 468 | 449 | 3.83 | 6.9 |  | 2.85 |
| Example 7 | 0.63 | 28.0 | 331 | 0.39 |  | 465 | 465 | 3.94 | 5.4 |  | 3.00 |
| Example 8 | 14.34 | 10.1 | 315 | 0.38 | 3.07 | 488 | 480 | 4.43 | 15.4 | ○ | 2.96 |
| Example 9 | 7.33 | 7.1 | 324 | 0.25 | 1.62 | 457 | 453 | 6.59 | 10.4 | ○ | 2.97 |
| Example 10 | 5.67 | 12.7 | 412 | 0.38 | 2.03 | 501 | 467 | 3.22 | 36.2 | ○ | 3.07 |
| Example 11 | 1.40 | 21.8 | 329 | 0.46 |  | 495 | 480 | 3.76 | 15.5 |  | 3.08 |
| Example 12 | 5.83 | 28.6 | 311 | 0.33 |  | 484 | 456 | 5.34 | 15.3 |  | 3.07 |
| Example 13 | 5.72 | 15.2 | 364 |  |  | 470 | 444 | 5.40 | 5.8 |  | 2.99 |
| Example 14 | 3.19 | 11.3 | 417 | 0.54 | 1.42 | 498 | 494 | 4.41 | 17.7 | ○ | 3.02 |
| Example 15 | 3.04 | 13.0 | 327 | 0.55 | 2.58 | 494 | 487 | 4.08 | 22.0 | ○ | 3.06 |
| Example 16 | 4.24 | 15.1 | 325 | 0.40 | 1.27 | 495 | 490 | 4.03 | 29.1 | ○ | 3.07 |
| Example 17 | 3.26 | 14.5 | 361 | 0.41 | 1.83 | 495 | 488 | 3.25 | 13.8 | ○ | 3.07 |
| Comparative Example 1 | 3.39 | 4.0 | ND | 0.78 | 4.28 | 500 | 494 | 6.68 | 3.5 | ○ | 3.02 |
| Comparative Example 2 | 1.64 | 4.8 | 386 | 0.71 | 3.20 | 474 | 464 | 6.21 | 7.3 |  | 3.06 |

ND: Not detected in dynamic visco-elasticity measurement (measurement range: room temperature to 450° C.).

What is claimed is:

1. A polyesterimide precursor having a repeating unit expressed by General Formula (2):

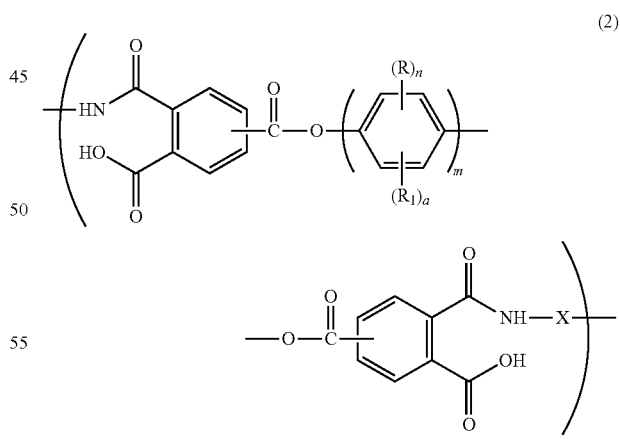

(2)

wherein R represents a phenyl group, $R_1$ represents an alkyl group with 1 to 6 carbon atoms or alkoxy group with 1 to 6 carbon atoms, n each independently takes an integer of 0 to 4, m is an integer of 2 to 4, a each independently takes an integer of 0 to 4; where not all n's are 0 at the same time and 0≤n+a≤4 is satisfied by each phenylene group, and X represents a divalent aromatic group and/or aliphatic group and the ester group is bonded at the meta- or para-position relative to the amide bond.

2. A polyesterimide precursor according to claim 1, whose intrinsic viscosity is in a range of 0.1 to 20.0 dL/g.

3. A polyesterimide having a repeating unit expressed by General Formula (3):

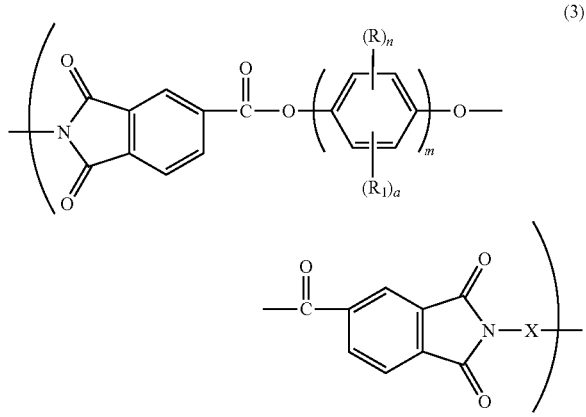

wherein R represents a phenyl group, $R_1$ represents an alkyl group with 1 to 6 carbon atoms or alkoxy group with 1 to 6 carbon atoms, n each independently takes an integer of 0 to 4, m is an integer of 2 to 4, a each independently takes an integer of 0 to 4; where not all n's are 0 at the same time and $0 \leq n+a \leq 4$ is satisfied by each phenylene group, and X represents a divalent aromatic group and/or aliphatic group.

4. A polyesterimide precursor according to claim 1, wherein n is 0, 1, or 2.

5. A polyesterimide according to claim 3, wherein n is 0, 1, or 2.

6. A polyesterimide precursor according to claim 1, wherein the number of R substitutions in the entire p-polyphenylene group is 1 to 4.

7. A polyesterimide according to claim 3, wherein the number of R substitutions in the entire p-polyphenylene group is 1 to 4.

8. A polyesterimide precursor according to claim 6, wherein the number of R substitutions in the entire p-polyphenylene group is 1 to 2.

9. A polyesterimide according to claim 7, wherein the number of R substitutions in the entire p-polyphenylene group is 1 to 2.

10. A polyesterimide precursor according to claim 6, wherein the number of R substitutions in the entire p-polyphenylene group is 1 or 2, where, if there are two or more R substitutions in the entire p-polyphenylene group, the number of R substitutions in the entire p-polyphenylene group is m or less and n in each phenylene group is 0 or 1.

11. A polyesterimide according to claim 7, wherein the number of R substitutions in the entire p-polyphenylene group is 1 or 2, where, if there are two or more R substitutions in the entire p-polyphenylene group, the number of R substitutions in the entire p-polyphenylene group is m or less and n in each phenylene group is 0 or 1.

* * * * *